United States Patent
Howell et al.

(10) Patent No.: US 12,036,129 B2
(45) Date of Patent: Jul. 16, 2024

(54) DEPLOYABLE COMPLIANT MECHANISM

(71) Applicant: Brigham Young University (BYU), Provo, UT (US)

(72) Inventors: Larry L. Howell, Orem, UT (US); Collin Ynchausti, Provo, UT (US); Anton E. Bowden, Lindon, UT (US); Nathan Brown, Orem, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 17/445,017

(22) Filed: Aug. 13, 2021

(65) Prior Publication Data
US 2022/0047397 A1    Feb. 17, 2022

Related U.S. Application Data
(60) Provisional application No. 63/065,464, filed on Aug. 13, 2020.

(51) Int. Cl.
*A61F 2/44*    (2006.01)
*A61F 2/30*    (2006.01)
*A61F 2/46*    (2006.01)

(52) U.S. Cl.
CPC .......... *A61F 2/442* (2013.01); *A61F 2/30942* (2013.01); *A61F 2/4455* (2013.01); *A61F 2/468* (2013.01); *A61F 2002/30522* (2013.01); *A61F 2002/30943* (2013.01)

(58) Field of Classification Search
CPC ............ A61F 2/442; A61F 2002/30522; A61F 2002/30069; A61F 2002/30485; A61F 2002/30556; A61F 2002/30092; A61F 2002/30563; A61F 2002/30579; A61F 2002/30985; A61F 2/4425; A61F 2/4455; A61F 2/446; A61F 2/4465; A61F 2/447
See application file for complete search history.

(56) References Cited

U.S. PATENT DOCUMENTS
7,537,617 B2 *   5/2009   Bindsell ............ A61F 2/28
                                                  623/17.11
9,060,876 B1 *   6/2015   To .................. A61F 2/442
(Continued)

FOREIGN PATENT DOCUMENTS
WO    WO-0193785 A2 *   12/2001   ............. A61F 2/442
WO    WO-2007084239 A2 *   7/2007   ......... A61B 17/8858
(Continued)

*Primary Examiner* — Ellen C Hammond
*Assistant Examiner* — Anna V. Little
(74) *Attorney, Agent, or Firm* — Brake Hughes Bellermann LLP

(57) ABSTRACT

Deployable Euler Spiral Connectors (DESCs) are introduced as compliant deployable flexures that can span gaps between segments in a mechanism and then lay flat when under strain in a stowed position. This paper presents models of Euler spiral beams combined in series and parallel that can be used to design compact compliant mechanisms. Constraints on the flexure parameters of DESCs are also presented. Analytic models developed for the force-deflection behavior and stress were compared to finite element analysis and experimental data. A spinal implant and a linear ratcheting system are presented as illustrative applications of DESCs.

26 Claims, 18 Drawing Sheets

(56) References Cited

U.S. PATENT DOCUMENTS

| | | | | |
|---|---|---|---|---|
| 2002/0022887 | A1* | 2/2002 | Huene | A61F 2/4611 623/908 |
| 2003/0014112 | A1* | 1/2003 | Ralph | A61F 2/442 623/17.13 |
| 2003/0078667 | A1* | 4/2003 | Manasas | B22F 10/20 623/17.15 |
| 2003/0171813 | A1* | 9/2003 | Kiester | A61F 2/447 623/17.11 |
| 2004/0010315 | A1* | 1/2004 | Song | A61F 2/4455 623/1.18 |
| 2004/0021123 | A1* | 2/2004 | Howell | F16F 1/027 251/337 |
| 2006/0100706 | A1* | 5/2006 | Shadduck | A61B 17/7098 623/17.11 |
| 2006/0149381 | A1* | 7/2006 | Kim | A61F 2/442 623/17.13 |
| 2006/0247781 | A1* | 11/2006 | Francis | A61F 2/442 606/78 |
| 2007/0173940 | A1* | 7/2007 | Hestad | A61F 2/441 623/17.12 |
| 2007/0270959 | A1* | 11/2007 | Dubousset | A61F 2/442 623/17.11 |
| 2008/0077246 | A1* | 3/2008 | Fehling | A61F 2/442 623/17.13 |
| 2008/0167718 | A1* | 7/2008 | Protopsaltis | A61F 2/442 623/17.11 |
| 2008/0183204 | A1* | 7/2008 | Greenhalgh | A61B 17/8858 606/198 |
| 2008/0281346 | A1* | 11/2008 | Greenhalgh | A61F 2/4455 606/191 |
| 2009/0024217 | A1* | 1/2009 | Levy | A61F 2/4455 623/17.16 |
| 2009/0222100 | A1* | 9/2009 | Cipoletti | A61F 2/447 606/90 |
| 2010/0082109 | A1* | 4/2010 | Greenhalgh | A61F 2/447 623/17.15 |
| 2010/0185291 | A1* | 7/2010 | Jimenez | F16F 1/025 623/17.16 |
| 2010/0209184 | A1* | 8/2010 | Jimenez | E05D 1/02 403/291 |
| 2011/0093075 | A1* | 4/2011 | Duplessis | A61F 2/4425 623/17.16 |
| 2012/0078313 | A1* | 3/2012 | Hasse | A61F 2/442 606/53 |
| 2012/0245557 | A1* | 9/2012 | Albrechtsen | A61M 5/3129 604/506 |
| 2015/0100125 | A1* | 4/2015 | Protopsaltis | A61F 2/4455 623/17.15 |
| 2016/0206439 | A1* | 7/2016 | To | A61F 2/442 |
| 2016/0213483 | A1* | 7/2016 | To | A61F 2/447 |
| 2016/0361177 | A1* | 12/2016 | Biedermann | A61F 2/442 |
| 2018/0256361 | A1* | 9/2018 | Bishop | A61F 2/30767 |
| 2019/0226814 | A1* | 7/2019 | Howell | E06B 9/06 |
| 2019/0343651 | A1* | 11/2019 | Ryan | A61F 2/4455 |
| 2020/0008827 | A1* | 1/2020 | Dearden | B25J 15/0233 |
| 2020/0046515 | A1* | 2/2020 | To | A61F 2/442 |
| 2020/0289285 | A1* | 9/2020 | Siemionow | A61B 17/7064 |

FOREIGN PATENT DOCUMENTS

| | | | | |
|---|---|---|---|---|
| WO | WO-2011028575 | A2 * | 3/2011 | ......... A61B 17/7026 |
| WO | WO-2018052939 | A1 * | 3/2018 | ............ A61B 17/29 |

* cited by examiner

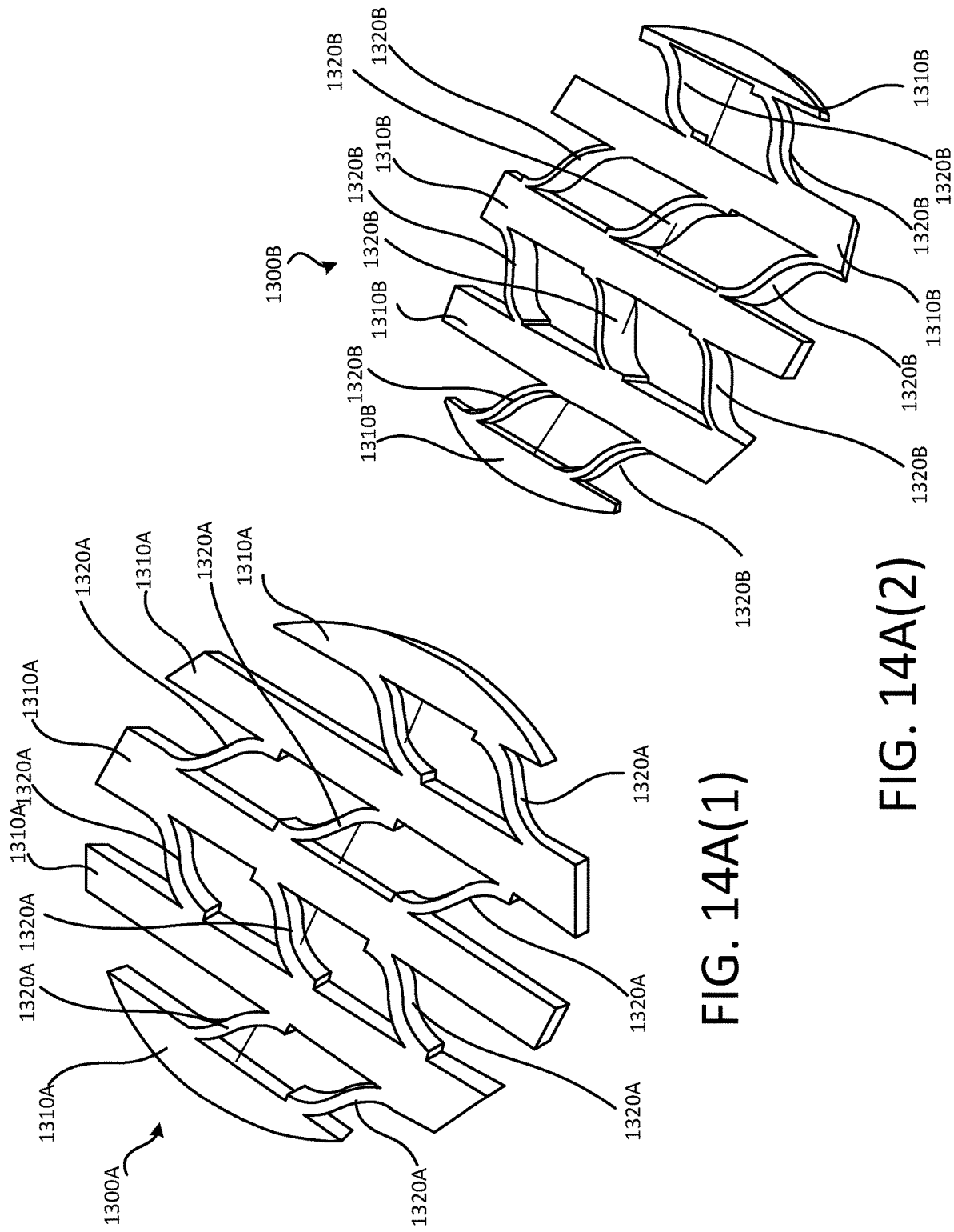
FIG. 14A(1)
FIG. 14A(2)

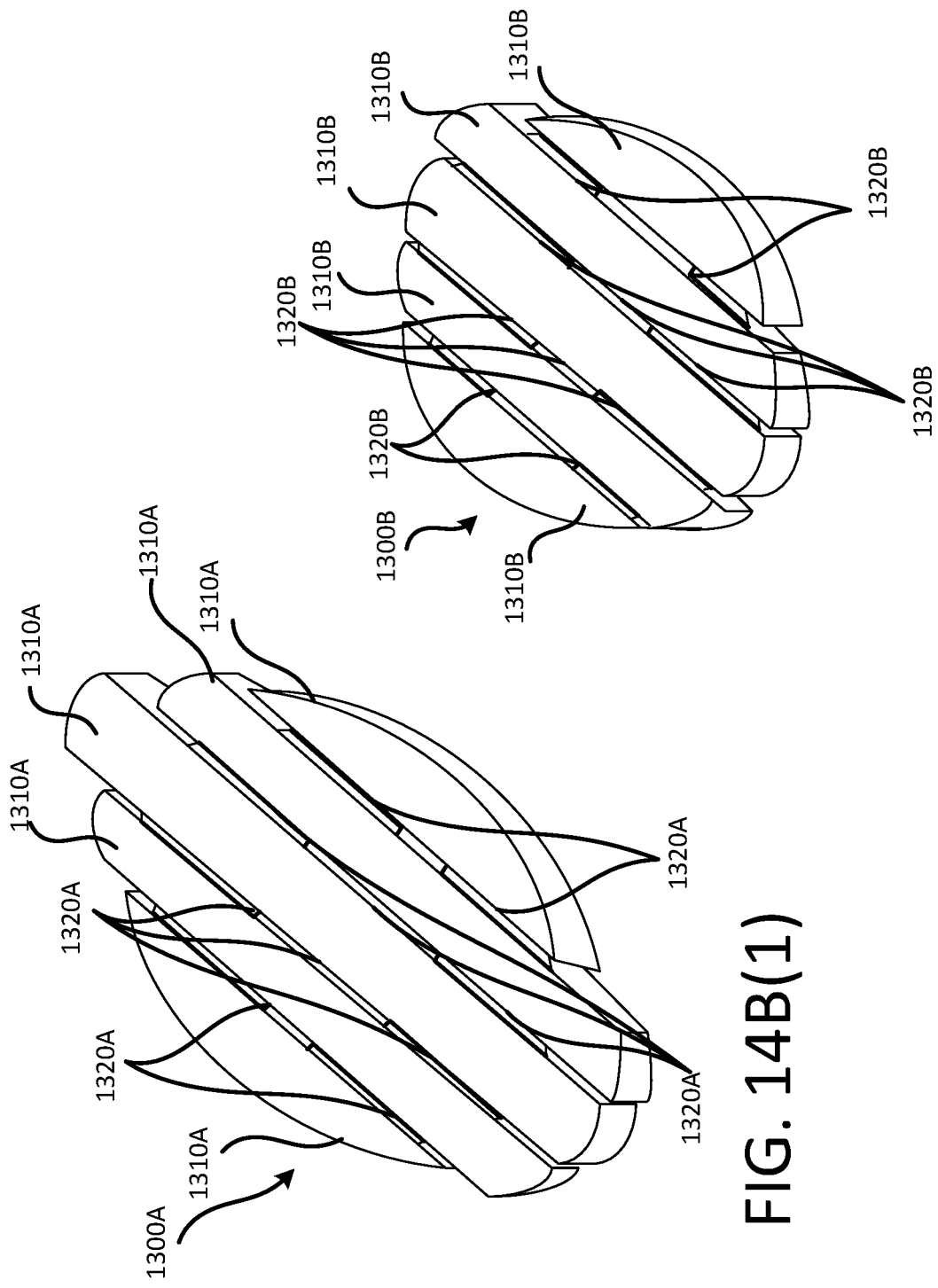
FIG. 14B(1)
FIG. 14B(2)

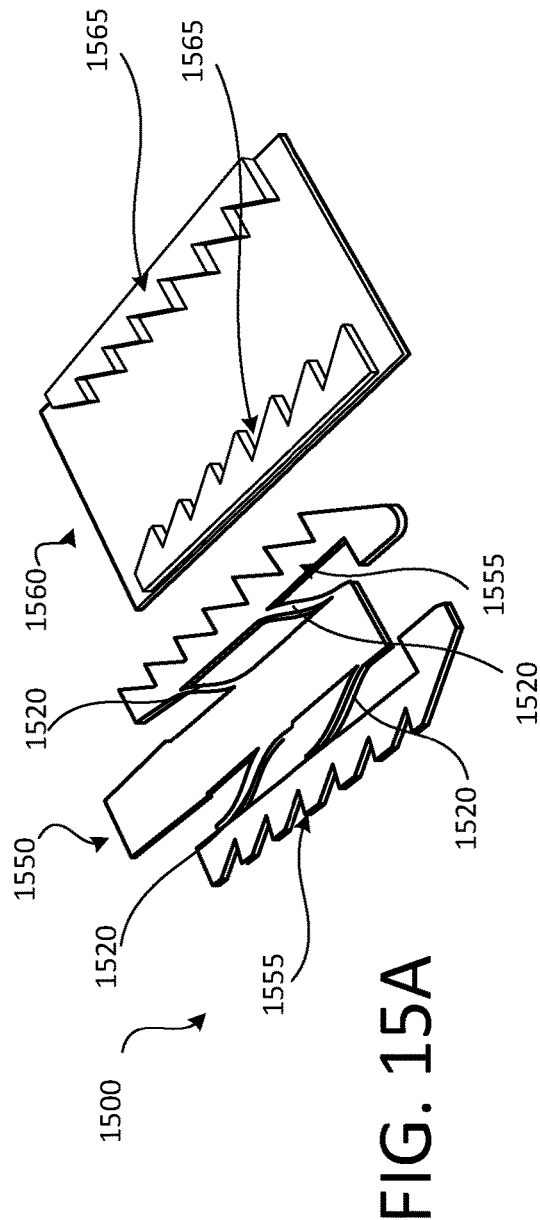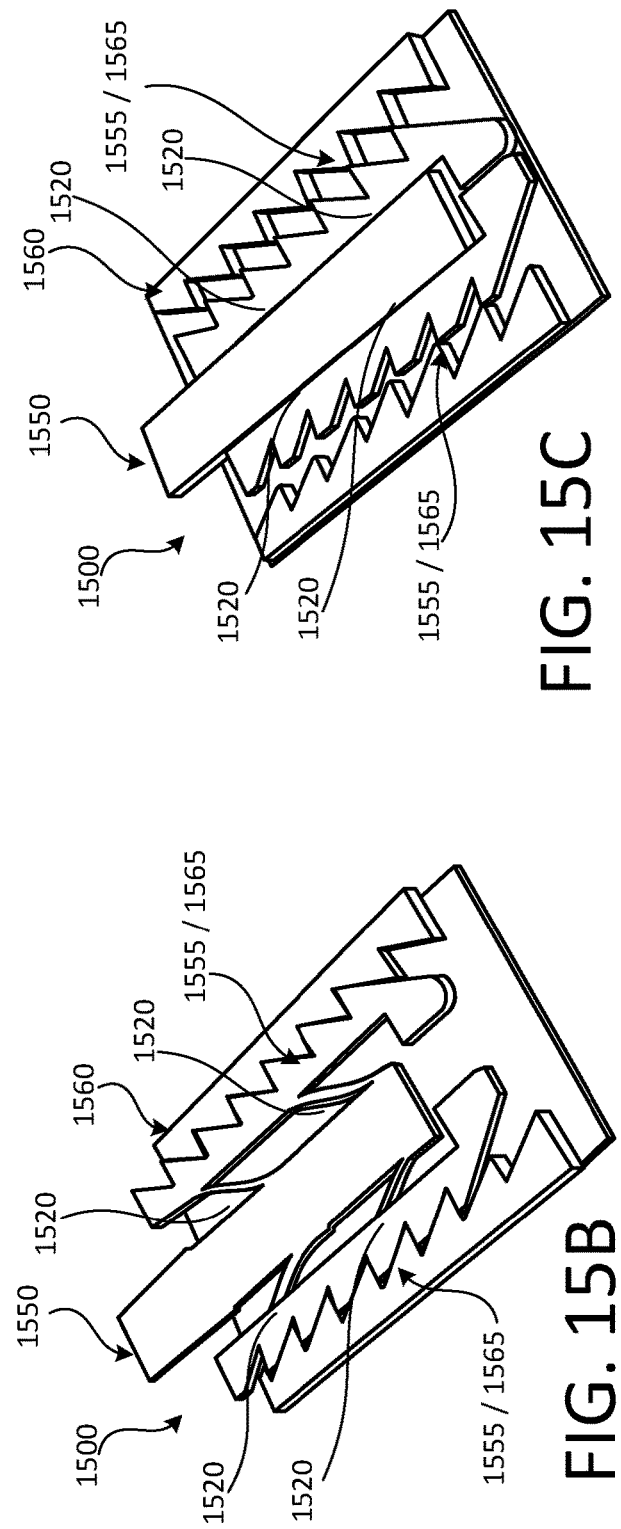

DEPLOYABLE COMPLIANT MECHANISM

CROSS-REFERENCE TO RELATED APPLICATION

This application claims priority to U.S. Provisional Application No. 63/065,464, filed on Aug. 13, 2020, entitled "DEPLOYABLE COMPLIANT MECHANISM SPINAL IMPLANT," the disclosure of which is incorporated by reference herein in its entirety.

STATEMENT REGARDING FEDERALLY SPONSORED RESEARCH

This invention was made with government support under Grant Number 1240417 awarded by the National Science Foundation. The government has certain rights in the invention.

TECHNICAL FIELD

This description relates in general to deployable compliant devices and structures that can be placed in a compact state and deployed to a larger state, and in particular, to medical devices and equipment that can be placed in a compact state and deployed to a larger state.

BACKGROUND

Devices and structures that can be placed in a compact state and deployed to a larger size may be desirable in many applications. One area of application of these types of devices is medical equipment, where an increase in use of minimally invasive surgeries has led to a desire for implantable devices to become smaller. In some situations, decreases in size, particularly in implantable devices, can lead to, for example, greater subsidence of bone due to less interface area between the implantable device and the bone. Similarly, it may be desirable to design space systems which can be stored and transported compactly, and deployed to the needed configuration.

SUMMARY

In one general aspect, an expandable implantable device includes a body. The body may include a plurality of support members and a plurality of compliant connectors connecting adjacent support members of the plurality of support members.

In some implementations, the plurality of support members are movable relative to each other in response to an externally applied force, between a first configuration and a second configuration. In some implementations, the first configuration is a deployed configuration in which adjacent support members of the plurality of support members are spaced apart from each other. In some implementations, the second configuration is a stowed configuration in which each of the plurality of support members substantially abuts an adjacent support member of the plurality of support members. In some implementations, the plurality of compliant connectors maintains a relative position of the plurality of support members so as to maintain the device in the first configuration or the second configuration.

The details of one or more implementations are set forth in the accompanying drawings and the description below. Other features will be apparent from the description and drawings, and from the claims.

BRIEF DESCRIPTION OF THE DRAWINGS

FIG. 14A illustrates example spinal implant devices in a deployed state. The example device shown in FIG. 14A(1) has a substantially circular cross-section in the deployed state, and the example device shown in FIG. 14A(2) has a substantially oval cross-section in the deployed state.

FIGS. 14B(1) and 14B(2) illustrate the example spinal implant devices shown in FIGS. 14A(1) and 14A(2), respectively, in a stowed state.

FIG. 15A illustrates a linear ratchet mechanism employing deployable Euler spiral connectors.

FIGS. 15B and 15C illustrate the linear ratchet mechanism shown in FIG. 15A, with a pawl inserted into a rack of the ratchet.

DETAILED DESCRIPTION

Figure 1:
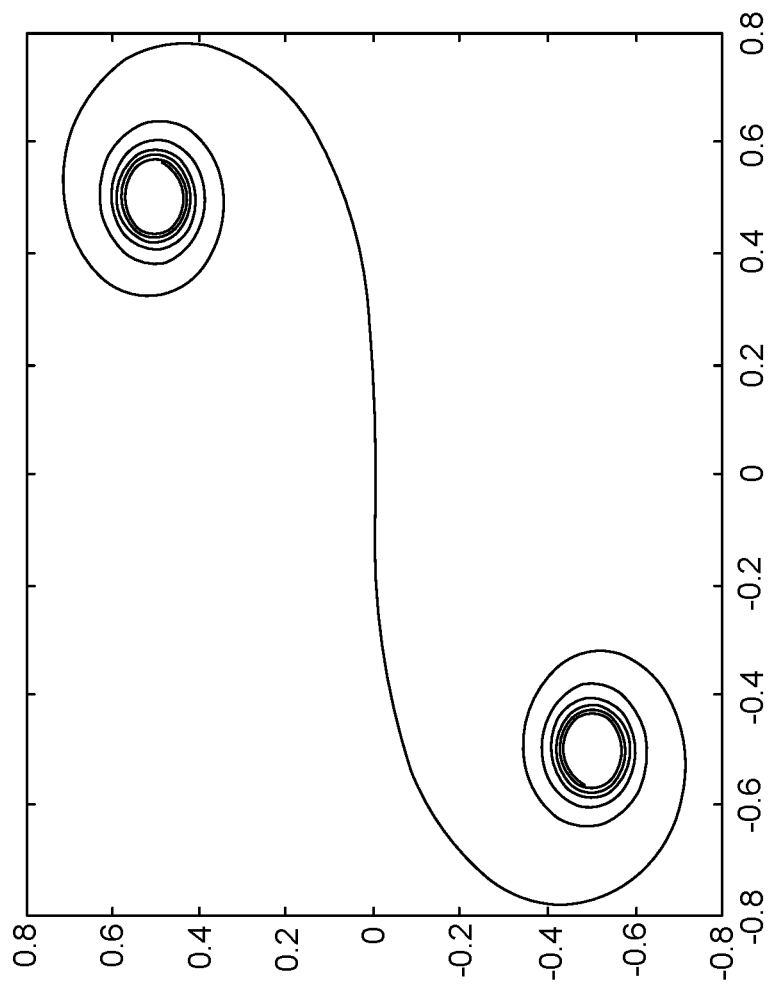
FIG. 1 illustrates an example Euler spiral.

The fields of origami-inspired engineering design and compliant mechanisms may present many useful solutions to common problems in engineering design, including, for example, creating designs that can achieve two or more states, and having these two states be a very compact state and a deployed, larger state. Additionally, the use of compliant mechanisms can be beneficial to deployable devices and structures because they can go through relatively large deflections and store strain energy within their flexible members which can be used for the actuation of the device. Although flexible members under load store strain energy that can be useful for deployment, their strained shape is largely determined by loads, boundary conditions, material properties, and geometry. The typical shape used to meet these requirements is unlikely to be compact. This presents an opportunity to develop concepts for shapes that, inspired by origami design, have a more compact stowed volume. In determining a candidate shape for a flexible member that will deflect into a compact volume, an Euler spiral, a curve that exhibits a linear change of curvature along its arc length, is a potential candidate. A flexible member having this type of shape may lie flat when a force is applied at its end. A compliant segment based on the Euler spiral could connect rigid segments and enable them to stow flat.

In some implementations, deployable Euler Spiral Connectors (DESCs) may be considered compliant deployable flexures that can span gaps between segments in a mechanism and then lay flat when under strain in a stowed position. Some implementations may make use of models of Euler spiral beams combined in series and parallel that can be used to design compact compliant mechanisms, and/or constraints on the flexure parameters of DESCs. In some implementations, analytic models developed for determination of the force-deflection behavior and stress were compared to finite element analysis and experimental data. A compliant flexure based on combinations of Euler spirals, or DESC, that allows a device to achieve a compact, stowed state with stored strain energy that can be released for deployment is presented herein. A spinal implant and a linear ratcheting system are presented herein, as illustrative applications of DESCs, simply for purposes of discussion and illustration. However, the principles to be described herein may be applied to other systems which may benefit from having a relatively compact stowed state, and are deployable to larger deployed state.

As noted above, origami-inspired design produces mechanisms that may be applied to, for example, packaging designs, aerospace and space-application designs, structural and disaster management designs, robotics, medical device designs, and other such design applications in which a stowed state and different deployed state of the device are desirable. Other applications in which deployable designs may be desirable may include, for example, antennas and reflectors, deployable gliders, ballistic barriers, train fairings, aquatic animal capturers and the like. Deployable designs can be achieved using, for example, origami patterns, shape memory polymers, spatial linkages, developable mechanisms, motorized joints, coils of flexible materials, inflation, telescoping pieces, pinned joints, scissor-like elements, and the like. Some deployable mechanisms may rely on the use of rigid-body members, while others may make use of compliant flexures.

Compliant mechanisms can be beneficial in these applications because they gain at least some of their motion from compliant, or flexible, members. These flexible members can be designed to enable a desired deflection and a desired reaction force. Compliant mechanisms store energy within their flexures as they deform and this strain energy can be released to deploy the mechanism when the holding force is released. The strain energy can be used as a basis for actuation of the mechanisms, reducing the complexity of actuation. With the use of compliant mechanisms and ideas derived from origami, a shape that will provide a highly efficient stowed volume can be determined.

An Euler spiral is a spiral with curvature that is a linear function of the arc length (e.g., K=Cs, where C is a constant and s is a distance along an arc-length). The spiral was originally developed to solve the *elastica* problem posed by Bernoulli, finding the curvature of a beam that would lay flat when a weight is placed on the beam end, but has also been used to solve other problems. It is also known as a Cornu Spiral, spiro, or clothoid. An example of an Euler spiral is shown in FIG. 1. The example Euler spiral shown in FIG. 1 was plotted using B=C($\alpha$)+iS($\alpha$), where C($\alpha$) and S($\alpha$) are Fresnel integrals, and $\alpha$ has a range of −5 to 5. The general equations for the x and y locations of a point on the spiral are shown in Equations (1) below, where C is a proportionality constant, a is the distance along the arc-length that the x and y position is desired, and $\theta(s)$ is the beam angle as a function of s, which in the case of an Euler spiral is $Cs^2$.

$$x=\int_0^\alpha \cos(\theta(s))ds=C\int_0^\alpha \cos(s^2)ds \quad y=\int_0^\alpha \sin(\theta(s))ds=C\int_0^\alpha \sin(s^2)ds \quad (1)$$

Because the curvature of the spiral is a linear function of the arc length, the curve creates a smooth, gradual transition. This characteristic may be beneficial in modeling, for example, intersection dynamics, designing roads and railroad tracks, performing curve-completion in graphics applications, and the like. Euler spirals were used to design lenticular stiffeners to provide additional stiffness to deployable space arrays where the stiffener would lay flat when stowed. The concept of the Euler spiral may be used to create a device that when stowed takes the least amount of space. The resulting equations are employed, extended, and validated hereinafter to create the DESC design.

Differences to be taken into account in this development may include geometry (DESCs are antisymmetric combinations of Euler spirals), motion (the lenticular stiffeners require sliding motion between adjacent panels), boundary conditions (DESCs are connected to both parallel panels), and system intent and corresponding performance metrics (lenticular stiffeners are meant to increase system stiffness while DESCs provide a means to guide an efficient deployment system). In implementations to be described herein, the spiral is used more for deployment stiffening and the loads applied to the spiral connections and device are out-of-plane. These differences result in differences in the geometry and behavior of the spiral.

DESC design will be shown with the governing constraint equations. The analytical force-deflection equation is also presented. Finite element analysis and experimental data will be presented to validate design equations. A discussion on the agreement of the analytical solutions with the experimental data will be presented. Example applications will be presented where the use of DESCs is beneficial.

Figure 2:
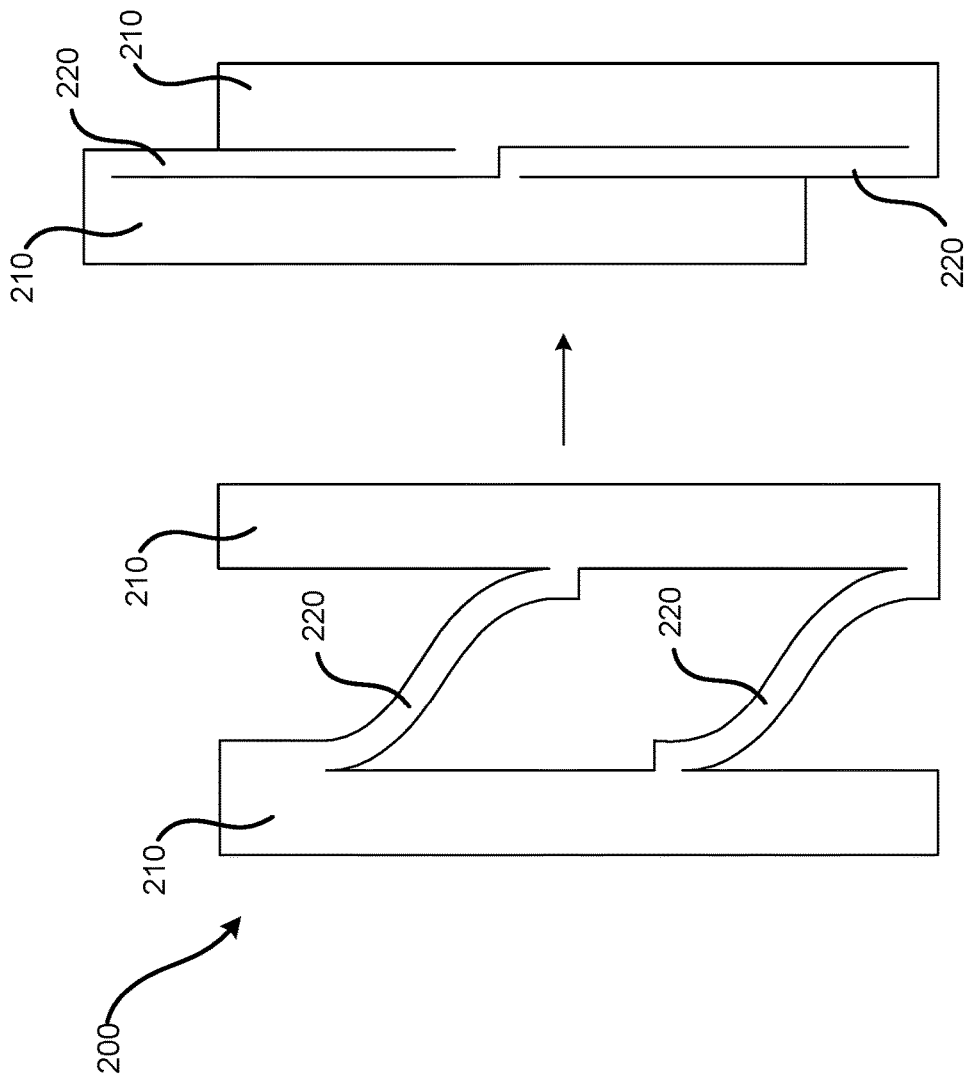
FIG. 2 illustrates two example parallel deployable Euler spiral connectors connecting two rigid segments of an example device.

An example Deployable Euler Spiral Connector (DESC) in accordance with implementations described herein, may be combined to connect two rigid bodies, as shown in FIG. 2. FIG. 2 illustrates two parallel DESCs defining compliant members 220 connecting two rigid segments 210 of a device 200. Both the deployed and the stowed configurations are shown. In this example, the compliant members 220 lay flat in the stowed configuration, resulting in an efficient stowed volume. The DESCs defining the compliant members 220 allow the device 200 to move from a deployed to stowed configuration. The DESCs defining the compliant members 220 span the distance between the deployed and stowed states, such that the DESCs defining the compliant members 220 act as connections between the rigid segments 210 and space filler when the device 200 is deployed. When the device 200 is being stowed, the DESCs defining the compliant members 220 may act as guiding mechanisms.

In some implementations, the connectors are manufactured in or past their deployed state, so their low energy state occurs when deployed. When the connectors are stowed, the energy input to stow them is transformed into strain energy in the connectors. When the stow force is released, the strain energy is released to move the connectors to their deployed, low energy, state.

Figure 3:
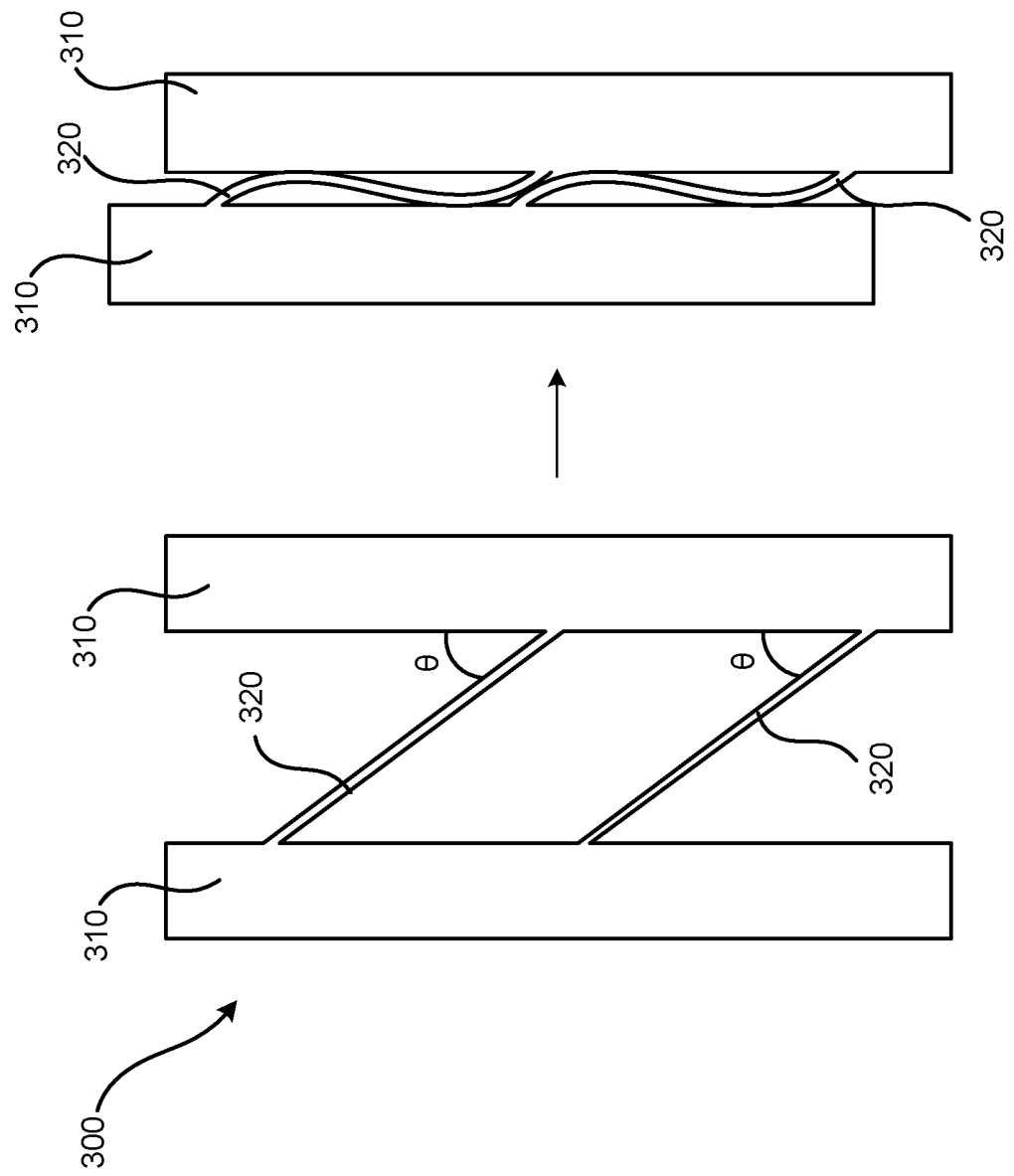
FIG. 3 illustrates two example parallel straight connections connecting two rigid segments of an example device.

To explain the behavior of the DESC flexures, the mechanical behavior of simpler connector geometries will first be examined. As one example, straight connectors 320 are shown in FIG. 3. For the straight connectors 320 to bridge a gap, they need to be connected between the rigid members 310 at angles between 0 and π/2 radians. When a device 300 with these connectors 320 is stowed, the connectors 320 bend and a part of them contacts the rigid members 310, therefore, the device 300 is not totally flat, as shown in FIG. 3. In particular, two parallel straight connectors 320 are shown connecting two rigid segments 310 of the device 300 in FIG. 3. Both the deployed (left) and stowed (right) configurations are shown. The connectors 320 do not lay flat in the stowed configuration, resulting in an ineffective use of space and higher stresses.

Figure 4:
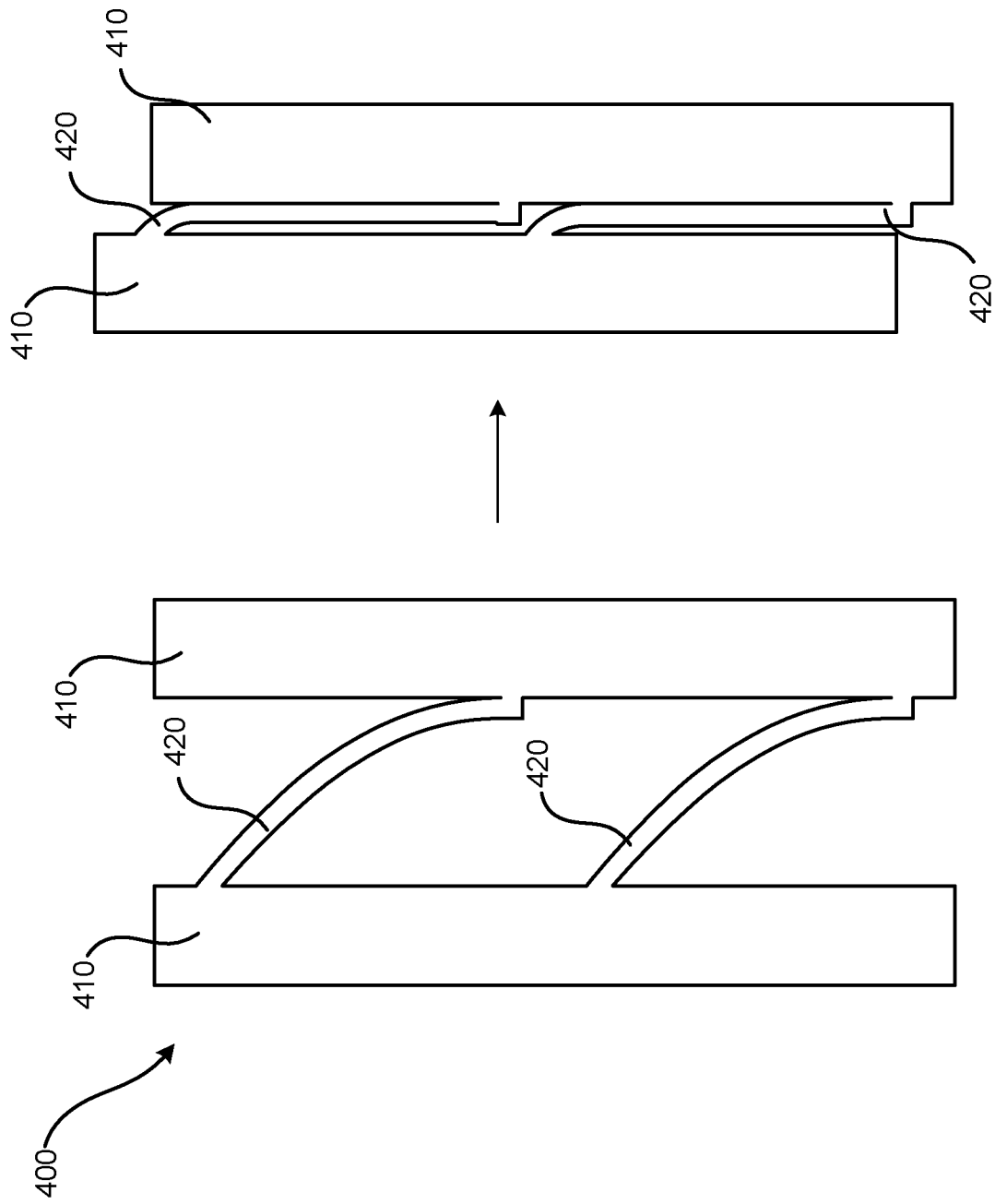
FIG. 4 illustrates an example mechanism using an Euler spiral connector.

If the connector shape used was only the shape of a single Euler spiral, one end of the connector 420 would not align parallel with the rigid member 410, as shown in FIG. 4, and the rigid members 410 would not lay flat. That is, in the example device 400 shown in FIG. 4 the left side of the connector 410 will not allow the device 400 to lay flat when stowed due to the attachment to the rigid member 410. If one end is not attached and allowed to slide, this may result in friction. Therefore, the DESC shape is antisymmetric Euler spirals connected at their points of zero curvature, as shown in FIG. 2. If the flexible segment is a DESC, it can be aligned with both ends parallel to the rigid members.

Thus, the Euler spiral equations were modified to define the desired antisymmetric geometry. In some implementations, the segment has an initial curvature, $\kappa_0$, at s=0, zero curvature at s=L/2, and curvature, $-\kappa_0$, at s=L. Applying these conditions with the fact that the curvature is a linear function of arc length, the curvature, $\kappa$, is defined as in Equation (2), and the proportionality constant, $\mu$, is as defined by Equation (3).

$$\kappa(s) = \mu\left(\frac{L}{2} - s\right) \tag{2}$$

$$\mu = \frac{2\kappa_0}{L} \tag{3}$$

In this arrangement, $\kappa_0$ is the initial (and maximum) curvature, s is the arc length between the origin and desired position on the curve, and L is the total arc length of the curve. The beam angle along the arc length, $\theta(s)$, is defined by Equation (4).

$$\theta(s) = \frac{\kappa_0}{L}(Ls - s^2) \tag{4}$$

Using the Taylor Series approximations for the sine and cosine in Equation (1) and substituting Equation (4) provides equations (5), (6), (7) and (8) to define the antisymmetric geometry.

$$\frac{x(s)}{L} = \frac{1}{L}\int_0^s \left(1 - \frac{\theta(s)^2}{2}\right)ds \tag{5}$$

$$\approx -\frac{p^5 q^2}{10} + \frac{p^4 q^2}{4} - \frac{p^3 q^2}{6} + p$$

$$\frac{y(s)}{L} = \frac{1}{L}\int_0^s \left(\theta(s) - \frac{\theta(s)^3}{6}\right)ds \tag{6}$$

$$\approx \frac{p^7 q^3}{42} - \frac{p^6 q^3}{12} + \frac{p^5 q^3}{10} - \frac{p^4 q^3}{24} - \frac{p^3 q}{3} + \frac{p^2 q}{2}$$

$$p = \frac{s}{L} \tag{7}$$

$$q = \kappa_0 L \tag{8}$$

These connections may span a desired distance in the x- and y-directions, so the final x- and y-coordinates are known, when s=L, then $x(s)=x(L)=x_{final}$, and $y(s)=y(L)=y_{final}$. At s=L, p=1 and Eqns. (5) and (6) can be simplified as shown in Equations (9) and (10). Equations (9) and (10) have four unknowns or design inputs: L, $\kappa_0$, x, and y. With the equations, two of the four design inputs need to be chosen to solve for the other two unknowns.

$$\frac{x(L)}{L} = -\frac{q^2}{10} + \frac{q^2}{4} - \frac{q^2}{6} + 1 \tag{9}$$

$$= -\frac{q^2}{60} + 1$$

$$\frac{y(L)}{L} = \frac{q^3}{42} - \frac{q^3}{12} + \frac{q^3}{10} - \frac{q^3}{24} - \frac{q}{3} + \frac{q}{2} \tag{10}$$

$$= -\frac{q^3}{840} + \frac{q}{6} = -\frac{q}{6}\left(\frac{q^2}{140} - 1\right)$$

Behaviors and mechanical limitations to take into account when designing DESCs will now be described. The force per unit width needed to fully flatten a lenticular stiffener is $$\overline{F} = \frac{\kappa_0 E t^3}{12 L_{ls}},$$

where E is the modulus of elasticity of the material, t is the in-plane thickness of the connector (see FIG. 5), and $L_{ls}$ is the arc length of the lenticular stiffener.

For a DESC of length L, composed of two spiral sections of length $$\frac{L}{2},$$

the DESC could be modeled as two springs in series, the force per unit width to compress the entire DESC is equal to the force per unit width to compress half the segment. Thus, the force per unit width to fully compress a DESC flexure may be defined by Equation (11). Using Equation (11) and defining the number of DESC flexures in parallel as n gives the total force as shown in Equation (12).

$$\overline{F}_{DESC} = \frac{\kappa_0 E t^3}{6L} \tag{11}$$

$$\overline{F}_{total} = n\frac{\kappa_0 E t^3}{6L} \tag{12}$$

Figure 5:
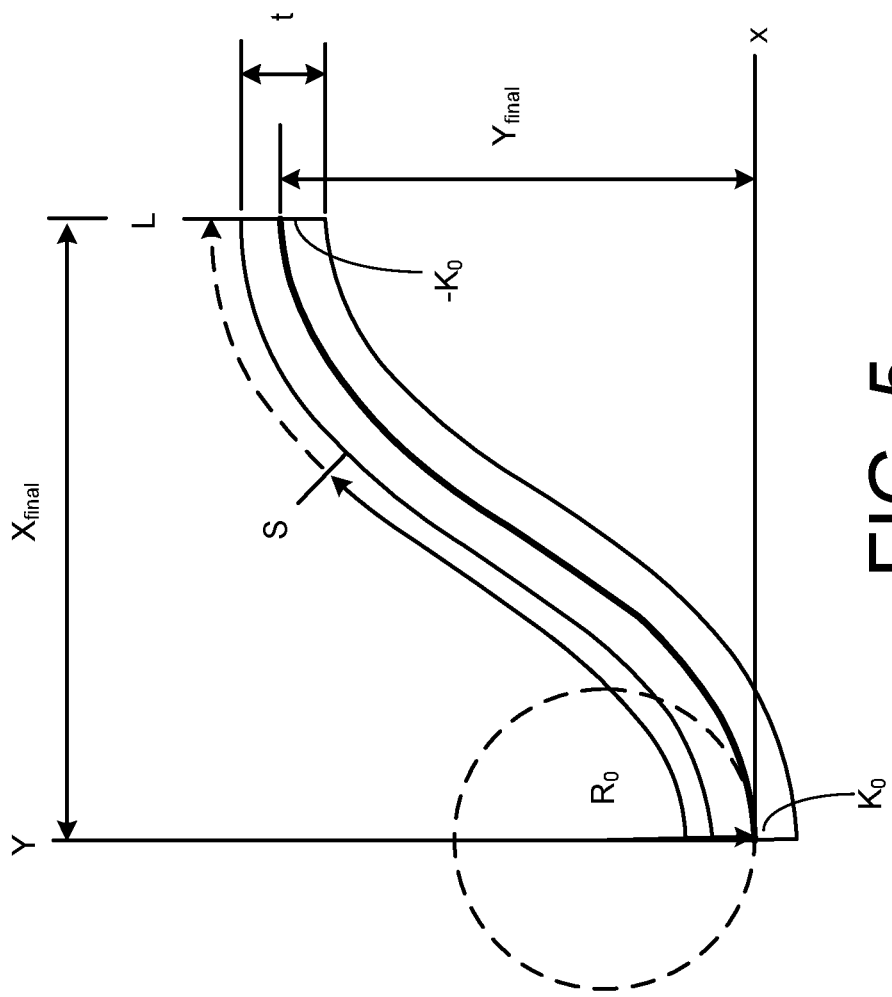
FIG. 5 illustrates key parameters for determining equations related to a deployable Euler spiral connector.

FIG. 5 presents some of the key parameters for determining the equations of the DESC. The distance along the arc length is defined as s and can vary from 0 to L, where L is the total arc length of the flexure. $X_{final}$ is the horizontal distance of the undeflected flexure, and Y is the vertical distance of the undeflected flexure. These distances represent the desired distances for the flexure to span. The initial (and maximum) curvature, $\kappa_0$ is also shown along with the circle of radius $R_0$ that defines the initial curvature ($\kappa_0=1/R_0$). The solid line represents the spiral. The shaded region represents the offset of the spiral in both directions to account for material thickness.

Figure 6:
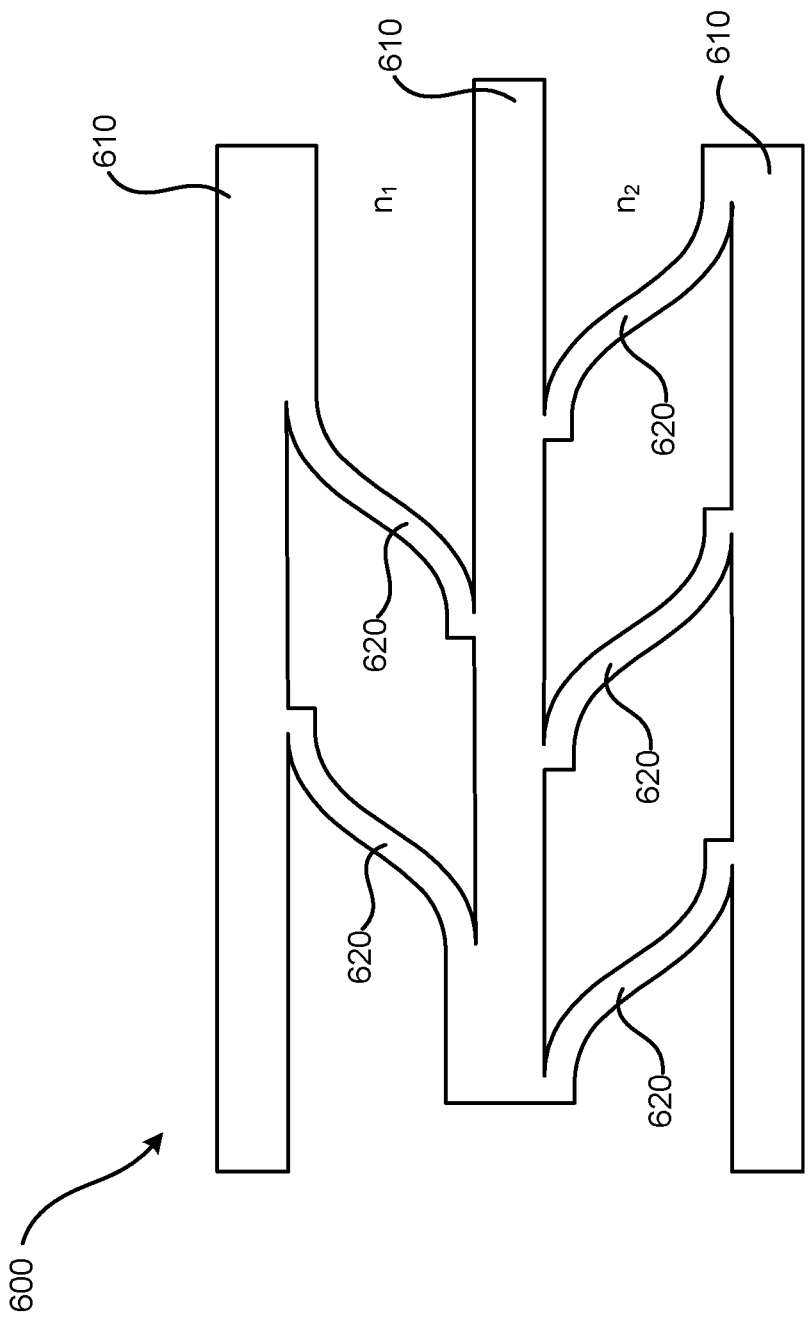
FIG. 6 illustrates an example mechanism with deployable Euler spiral connectors in parallel and in series.

For designs where there are DESC flexures in parallel and in series, Eqn. (12) is modified as shown in Equation (13), where $n_1$ is the number of DESCs in parallel in the top row and $n_2$ is the number of DESCs in parallel in the bottom row, as shown in FIG. 6. FIG. 6 illustrates an example mechanism 600 with DESCs defining compliant connectors 620 in parallel and series between rigid members 610. The top row has 2 ($n_1$) DESCs and the bottom row has 3 ($n_2$) DESCs in parallel.

$$\bar{F}_{total} = \frac{2n_1 n_2}{n_1 + n_2} \frac{\kappa_0 E t^3}{6L} \tag{13}$$

In solving the boundary value problem (BVP) of a force deflection curve, the curvature of a thin elastic beam may be defined by Equation (14), where Ki is the initial curvature of the beam, M is the moment on the beam, I is the area moment inertia of the beam, and E is as described above.

$$\kappa = \frac{d\theta}{ds} = \frac{M}{EI} + \kappa_i \tag{14}$$

Figure 7:
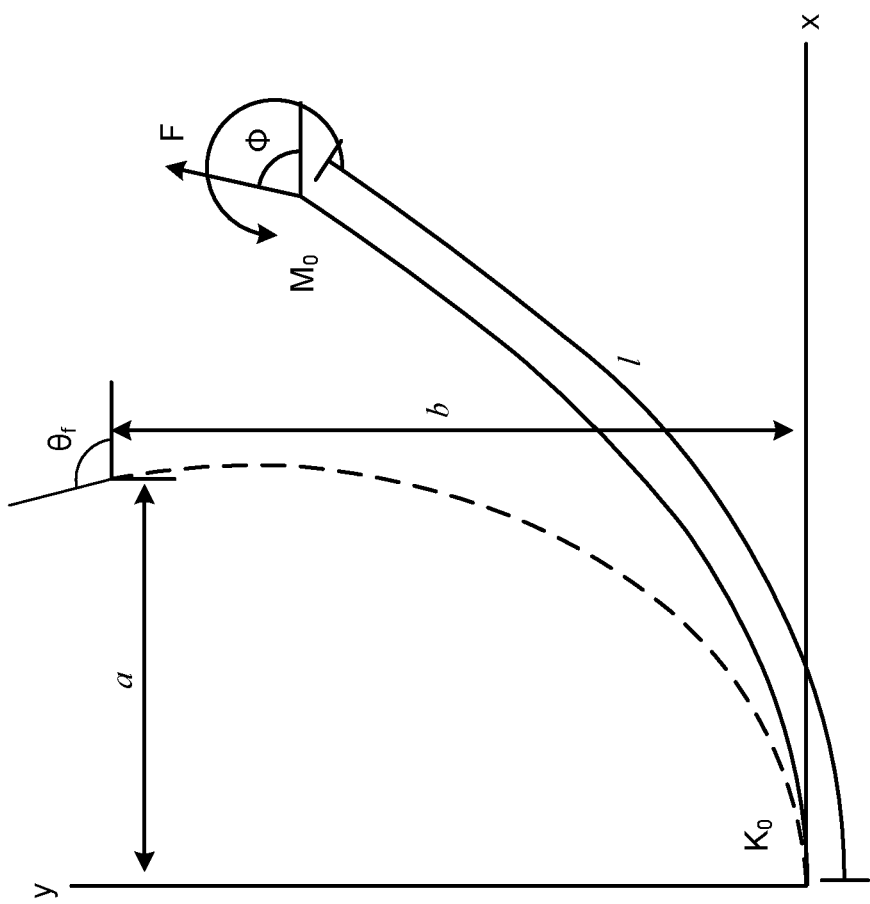
FIG. 7 illustrates a half Euler spiral model for derivation of a force-deflection curve.

The example beam shown in FIG. 7 has a moment load, $M_0$, and a force load, F, applied at an arbitrary angle, $\phi$. FIG. 7 illustrates a half DESC (Euler Spiral) model used in the derivation of the force-deflection curve. L is the arc length of the beam, $\kappa_0$ is the initial curvature of the beam, $\phi$ is the angle from the positive x-axis of the applied force, $\theta_f$ is the end point angle of the deflected beam, F is the applied force, $M_0$ is the applied moment, and a and b are the horizontal distance from the y-axis and the vertical distance from the x-axis to the beam end point, respectively. Arbitrarily cutting a segment of the beam and taking the moment, M, at the cut point yields Equation (15).

$$M = M_0 + F\sin\phi(a-x) - F\cos\phi(b-y) \tag{15}$$

Substituting Equation (15) for the moment, M and $$\kappa_i = \frac{\kappa_0}{l}(l-s)$$

into

Eqn. (14) yields the curvature as shown in Equation (16).

$$\theta s = \frac{F}{E}[\sin\phi(a-x) - \cos\phi(b-y)] + \frac{M_0}{EI} + \frac{\kappa_0}{l}(l-s) \tag{16}$$

Differentiating Eqn. (16) with respect to s yields Equation (17).

$$[2]\theta s = \frac{F}{EI}(-\sin\phi xs + \cos\phi ys) - \frac{\kappa_0}{l} \tag{17}$$

Substituting the identities $$\frac{dx}{ds} = \cos\theta \text{ and } \frac{dy}{ds} = \sin\theta$$

into the equation, and simplifying, produces Equation (18), with boundary conditions at the beam end defined by Equation (19).

$$[2]\theta s = \frac{F}{EI}\sin(\theta - \phi) - \frac{\kappa_0}{l} \tag{18}$$

$$\theta(0) = 0 \tag{19}$$

$$\theta'(l) = \frac{M_0}{EI}$$

Equation (18) can be solved using numerical integration methods and the beam endpoints, (a, b), can be determined for any given $M_0$, F, and $\phi$. Specifically in the case of the half DESC, in FIG. 7, a force is applied on the flexure in the negative y-direction $$\left(\phi = \frac{3\pi}{2} \text{ radians}\right)$$

and no moment is applied to the flexure ($M_0=0$), producing $\theta0'(l)=0$ for the second boundary condition in Equation (19). Due to the symmetric nature of the DESC (the DESC being the two antisymmetric half Euler Spirals), the displacements due to the force determined in the solution to Equation (18) can be doubled because the flexure acts as two springs in series. This provides the force-deflection relationships of the DESC.

In avoiding over-stress, the elastic strain limit may be taken into consideration. The maximum stress may be represented by $\sigma_{max}=(M_{max} t)/2I$, where $M_{max}$ is the maximum moment in the beam, and I is the area moment of inertia of the beam. According to the Euler-Bernoulli beam theory for thin elastic beams, $\kappa=M/EI$, where $\kappa$ and M are the curvature and moment, respectively, at a specific distance on the beam. The initial curvature, $\kappa_0$, may represent the maximum curvature of the DESC, therefore $\kappa_0=M_{max}/EI$. Rearranging this equation to solve for the maximum moment in terms of the curvature and substituting into the stress equation, the maximum stress, $\sigma_{max}$, for a DESC flexure results in Equation (20), which is consistent with results for lenticular stiffeners. Because the maximum curvature is located at the connections to the rigid segments, the maximum stress will occur at these locations.

$$\sigma_{max} = (\kappa_0 E_t)/2 \tag{20}$$

As can be seen in Equation (20), the stress is dependent on the material properties of the flexure, and the maximum curvature and thickness of the flexure. Having a non-dimensional parameter that provides a limit for what values the maximum curvature and thickness of the flexure can be without yielding due to stress would be a useful parameter to aid in the design of these flexures. Incorporating a safety factor, n, to the maximum stress in Equation (20) and equating this value to the yield strength, $S_y$, the non-dimensionalized product of the curvature and thickness, the elastic strain value ($\kappa_0$ t), can be solved as in Equation (21).

$$\kappa_0 t \leq 2/n(S_y/E) \tag{21}$$

This may provide a relatively straightforward parameter limit, defined here as the "elastic strain limit", that is particularly useful in designing DESCs that maintain stress below the yield strength. Equation (21) also illustrates that another important parameter for the curvature of the DESCs is the yield strength to Young's modulus ratio, $S_y/E$. If this ratio is high, higher initial curvatures to a constant flexure thickness are possible without plastic deformation of the flexure during the stowing motion.

In avoiding over-curvature, the critical curvature constant may be taken into consideration. Because the flexure's curvature is linearly proportional to the arc length of the flexure, the value of proportionality determines in what increments this linear change occurs. Equations (3) and (4) show the linear change is dependent on $$\frac{\kappa_0}{L}.$$

Figure 8:
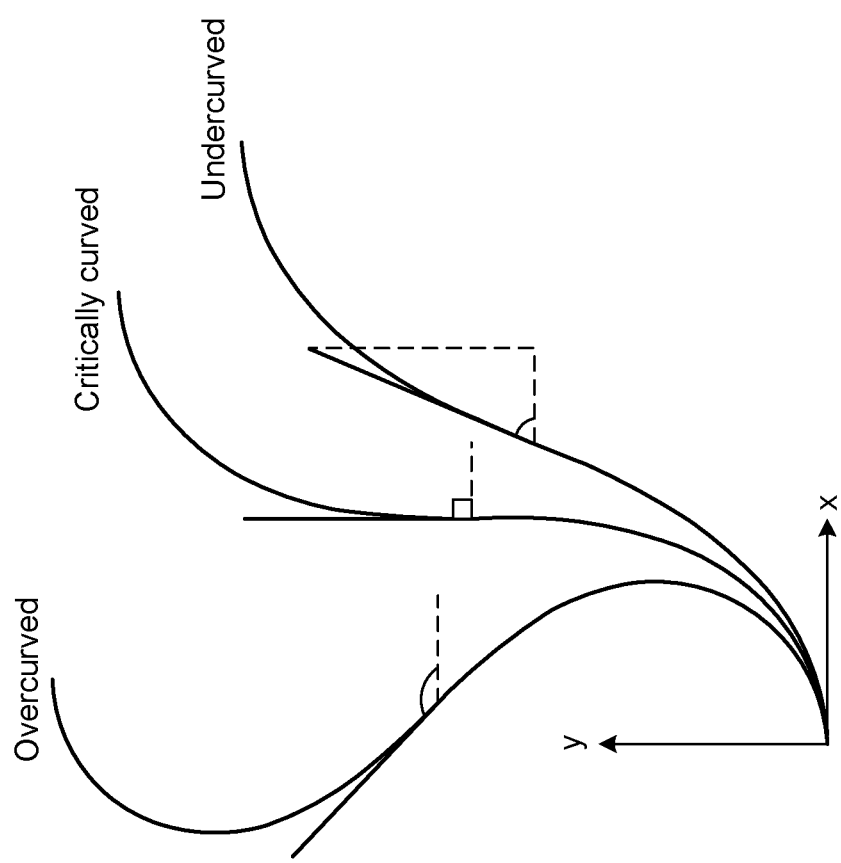
FIG. 8 illustrates different variations of curvature of a deployable Euler spiral connector.

This means that depending on the length of L, the increment at which the curvature changes may be smaller or larger. When L is smaller, then the proportionality is large and the change in curvature and angle along the beam has a larger change per unit length, while if L was larger, the inverse occurs. If L becomes too large compared to $\kappa_0$, the flexure can become overcurved. A flexure is overcurved if the slope ($\theta$) at the midpoint of the flexure is greater than $$\frac{\pi}{2}.$$

flexure whose angle at the midpoint is equal to $$\frac{\pi}{2}$$

is defined as critically curved. A flexure where the slope at the midpoint is less than $$\frac{\pi}{2}$$

is undercurved and desirable. In all these cases, the flexure is the shape of an Euler Spiral, however, an overcurved flexure will not lie flat when a vertical force is applied but will lie on itself, nullifying the purpose of the flexure. FIG. 8 illustrates different variations of curvature of a DESC. In this example, all three curves have the same maximum curvature, $\kappa_0$, with differing lengths, L.

The "critical curvature constant" is defined as the value where overcurvature begins to occur. Unlike the "elastic strain limit", this value is only dependent on the geometry of the flexure. To avoid overcurvature, the beam angle, $\theta(s)$, at the midpoint of the flexure ($s=L/2$) needs to be less than or equal to vertical ($\theta(L/2)$: $\pi/2$). Substituting these values into Eqn. (4) and solving for the non-dimensional product of the curvature and length, the equivalent curvature ($\kappa_0 L$), yields Equation (22).

$$\kappa_0 L \leq 2\pi \quad (22)$$

When using an approximation d to define the DESC flexure, another value of the critical curvature constant may be determined. Similar to the process above, the x portion of the parametric function (Equation (5)) was differentiated with respect to s to determine the equation of the beam angle. Then imposing the constraint that the change in x with respect to s needs to be greater than zero when $s=L/2$ ($dx/ds_{s=L/2} \geq 0$) produces Equation (23). With flexures that are critically curved or not extremely overcurved, the deflection of the flexure may or may not follow the normal DESC motion and lay flat upon an applied vertical load. Equation (23) helps to determine the limits to which flexures can be used without voiding the ability to lay flat.

$$\kappa_0 L \leq 4\sqrt{2} \approx 5.66 \quad (23)$$

Figure 9:
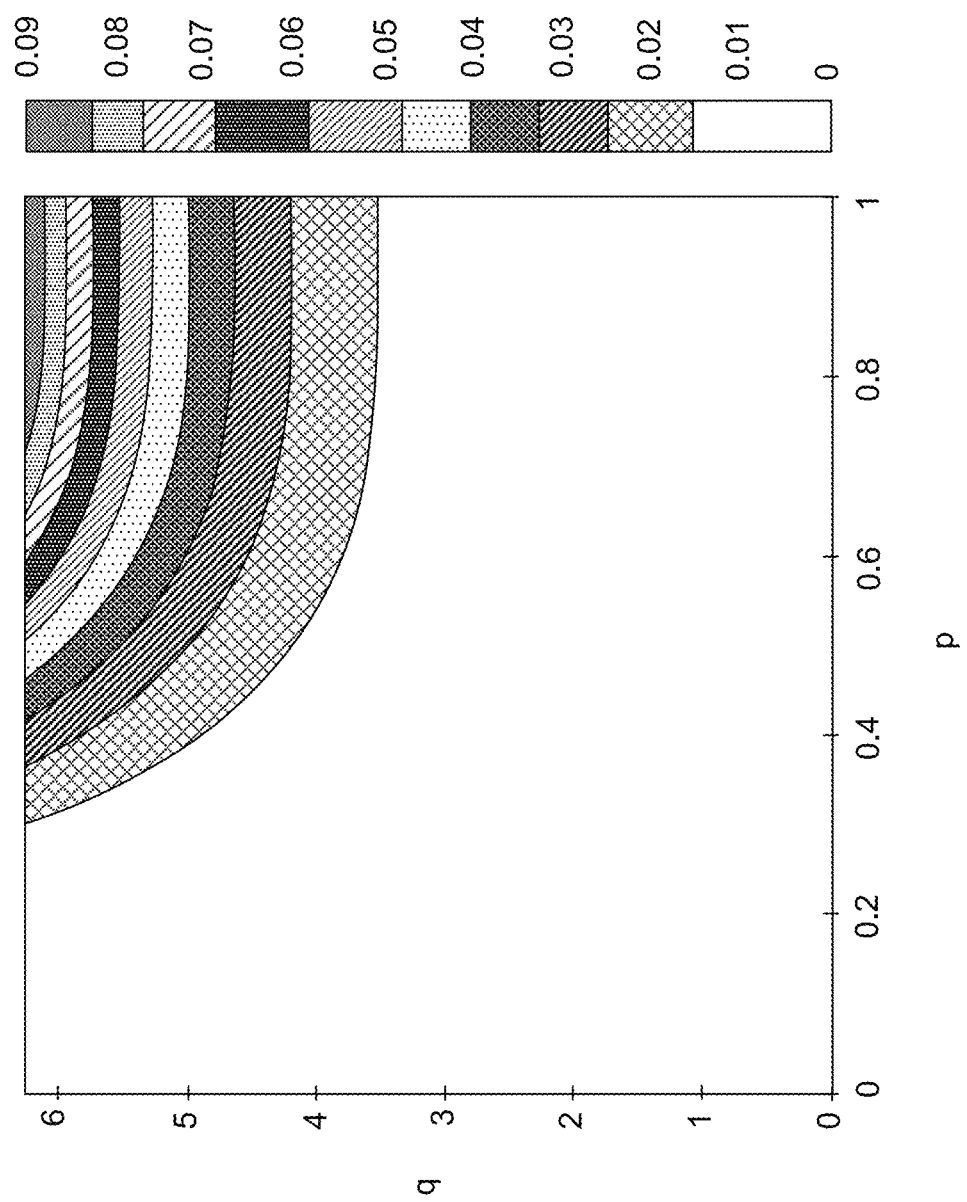
FIG. 9 illustrates an error plot.

The error of the spiral geometry due to the Taylor series approximation was determined by comparing the x(s)/L and y(s)/L values for the analytical solution and Taylor Series approximation for $p=0 \rightarrow 1$ and $q=0 \rightarrow 2\pi$, as this is the limiting factor for a DESC as shown in Section 3.2.4. The error is the distance between the exact and approximate points, calculated using Equation (24). FIG. 9 is a graph plotting the error for the above values of p and q. The maximum error using the Taylor Series approximations with q equal to $2\pi$ does not exceed 10%.

$$\text{error} = \sqrt{\left[\left(\frac{x(s)}{L}\right)-\left(\frac{x(s)}{L}\right)_{Taylor}\right]^2 + \left[\left(\frac{y(s)}{L}\right)-\left(\frac{y(s)}{L}\right)_{Taylor}\right]^2} \quad (24)$$

The case of the three DESCs in parallel provides a statically indeterminate situation. However, because the flexures are much thinner than the rigid members, the DESCs can be assumed to be the only piece of the device that is deflecting. And because the flexures lying flat is the main concern, the third DESC only contributes to an increase of the force needed to stow the device, as shown in Equations (12) and (13).

Because the motion of mechanisms using DESCs is dependent on the deflection of beams, considerations must also be taken during design to account for the amount of energy that will be stored within the flexure. While this energy is needed to stow the device, the benefit of using a compliant flexure is that a device with DESCs can be used to store strain energy. This stored strain energy can provide actuation for the device to move to the deployed state. This stored strain energy can also be used to provide a compact biasing force to increase precision in assemblies with clearances or can act as an ultra-compact spring in mechanical systems where space is at a premium.

In many cases, the number of cycles a DESC flexure will experience will be low because it is used for deployment, however, other cases may have higher cycles and a more detailed fatigue analysis. In these cases, Equation (20) can be used with appropriate fatigue failure theories to determine the limiting values of the flexure parameters to avoid fatigue failure.

DESC flexures were modeled in finite element analysis (FEA) software to evaluate the analytical models presented above. The flexural moduli were determined from the three-point bend tests (to be described in more detail below) listed in Table 1. With the moduli in Table 1, the theoretical force to fully stow each DESC, the force-deflection curve, and maximum stress in the flexure was determined using Equations (12), (18), and (20), respectively, and FEA was performed.

TABLE 1

| Thickness (mm) | Flexural Modulus of Elasticity (MPa) |
| --- | --- |
| 1 | 114 |
| 2 | 103 |
| 3.2 | 123 |

Figure 10A:
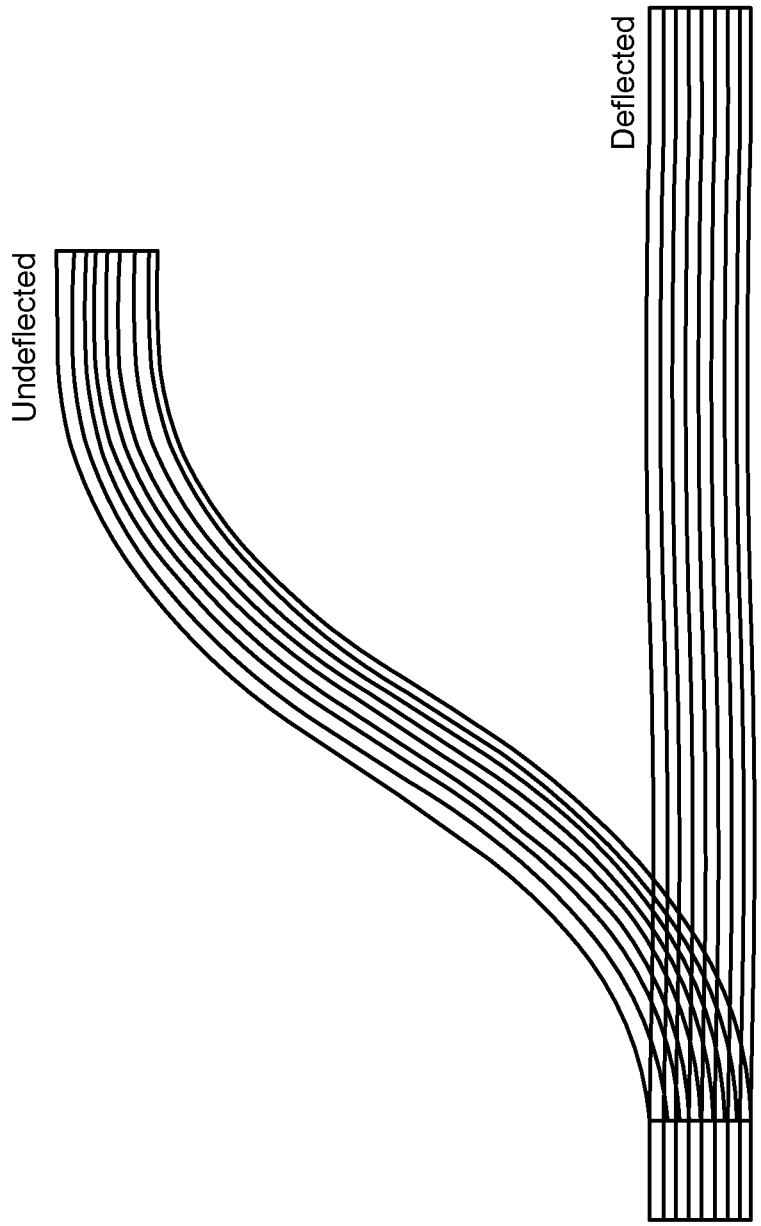
FIG. 10A illustrates a deflected state and an undeflected state of a deployable Euler spiral connector.
Figure 10B:
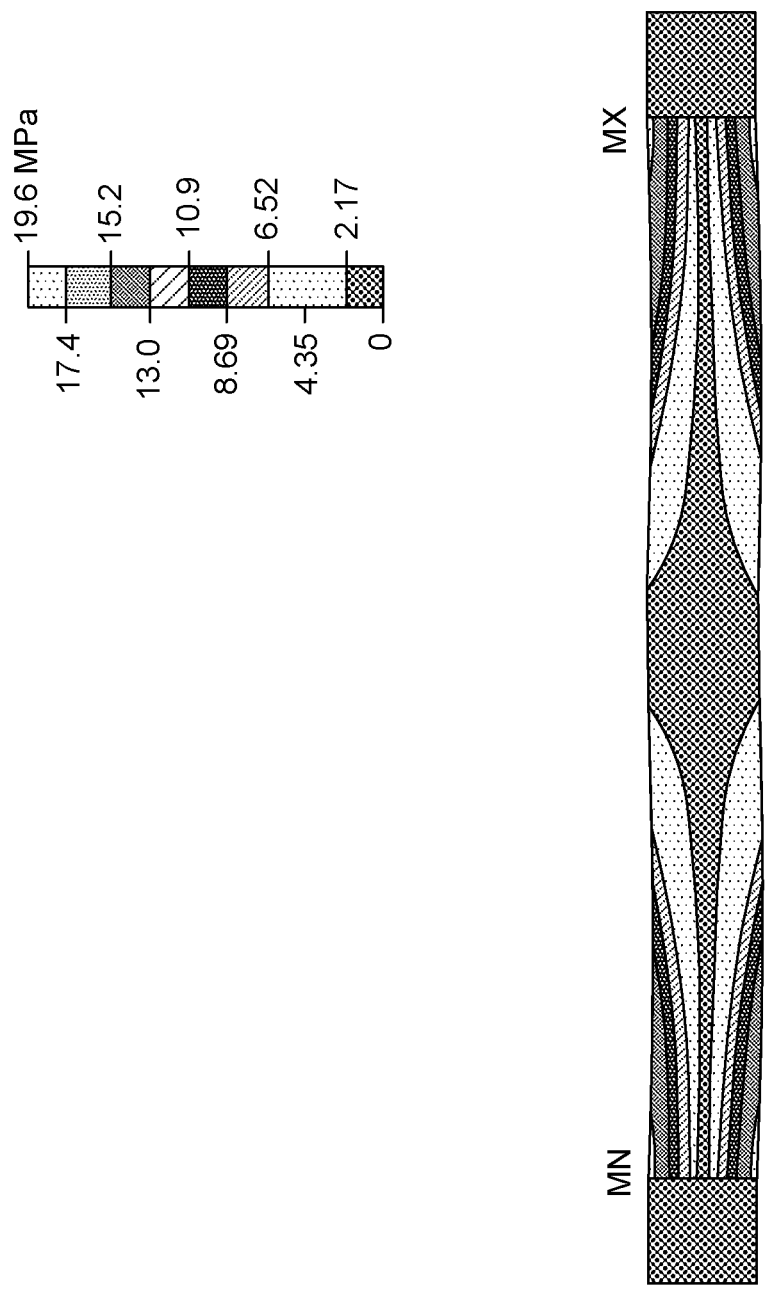
FIG. 10B illustrates a Von Mises stress distribution of a deployable Euler spiral connector.

Finite Element Analysis (FEA) was performed, using ANSYS Mechanical APDL, on a curve defining the spiral flexure with the parameters as shown in Table 2 below. The curve was meshed using BEAM188 elements. The section was split into 10×10 elements with each element being 0.1 mm long. All degrees of freedom (DOF) were constrained at the base of the flexure. The in-plane rotation of the top end of the flexure was constrained to zero and the y-displacement was set to −11.5 mm. Geometric nonlinearities were also included in the analysis. The reaction force and the Von Mises stress in the flexure were determined and are shown in Table 2. The flexure deflection and Von Mises stress distribution are shown in FIGS. 10A and 10B. As expected, the flexure lies essentially flat and the maximum stress occurs at the top and bottom of the flexure at its ends. FEA was also performed on curves of different parameters, shown in Table 2, using the same meshing parameters as described above. The results of these studies are also presented in Table 2.

To evaluate the accuracy of the presented models, the values of the force to stow, maximum stress, and maximum deflection of the DESCs were used to calculate the differences. The percent differences for the force to stow were calculated with the FEA value. The percent difference for the maximum stress was calculated with the FEA value being considered the true value. Because the force deflection curve was determined using the maximum force calculated from Equation (12), the difference in deflection was used to determine how accurate the models were. The value found using Equation (18) was used as the true value in this case.

TABLE 2

| 255 | | $\kappa_0 = 0.19$ rad/mm L = 19.9 mm | | $\kappa_0 = 0.39$ rad/mm L = 12.8 mm | |
| --- | --- | --- | --- | --- | --- |
| ptConfiguration | | t = 1 mm | t = 2 mm | t = 1 mm | t = 2 mm |
| ptForce to Stow (N/mm) | Eqn. (12) | 0.18 | 1.32 | 0.58 | 4.17 |
| | FEA | 0.19 | 1.33 | 0.61 | 4.2 |
| | Percent Difference (%) | 5.3 | 0.8 | 4.9 | 0.7 |
| ptMaximum Stress (MPa) | Eqn. (20) | 10.83 | 19.64 | 22.22 | 40.31 |
| | FEA | 11.10 | 19.60 | 22.8 | 38.70 |
| | Percent Difference (%) | 2.5 | 0.2 | 2.5 | 5.5 |
| ptMaximum Deflection (mm) | Y-Distance of Flexure | 11.50 | | 8.76 | |
| | Eqn. (18) | 11.31 | | 8.87 | |
| | Percent Difference (%) | 1.7 | | 1.2 | |

Table 2 shows the results of the models and FEA along with the comparisons of agreement between models and FEA. The percent difference between the models and the FEA is no greater than 5.5% in any of the cases for the force to stow, maximum stress, and the maximum deflection of the DESC. These results show that Equations (12), (18), and (20) provide reasonable predictions of the DESC behavior.

Physical testing of hardware was performed and compared to the analytical equations and FEA presented in this work to further discover the accuracy of the models. A three-point bend test was used to approximate the flexural modulus of elasticity of the material. DESC prototypes were also made and tested to determine the maximum stow force. Testing was performed on an Instron 3345 tensile tester with a position control resolution of 0.133 µm.

A three-point bed test was performed, in which flat rectangular bars of 1.0, 2.0, and 3.2 mm thicknesses were 3D printed in POLYFLEX (TPU95) to be used in a three-point bending test to determine the flexural modulus of elasticity of POLYFLEX. Ten samples of each thickness were manufactured and tested. The rectangular POLYFLEX bars were 3D printed with the thickness (y-direction) and length (x-direction) in the plane of the printer. The widths of the bars were printed in the z-direction to match the direction in which the DESC flexures were printed.

The three-point bend test setup, including a base and plunger were made according to dimensions listed in the ASTM D790 standard. Three different sized stationary bases were used with the three corresponding sample thicknesses. With the stationary base secured to the bottom of the fixture, the plunger was attached to the load cell and then mounted onto the cross head. For the 2 and 3.2 mm samples, the system was set up to measure the data using an Interface SMT1-22 98 N load cell with an uncertainty of 0.03 percent. For the 1 mm samples, the system was set up to measure the data using an Interface SMT1-1.1 5 N load cell with an uncertainty of 0.04 percent. After setup, the load cell was calibrated, and the displacement zeroed.

Each sample set was tested according to ASTM D790 and the load-displacement data was recorded. The force was zeroed between samples to ensure that the recorded force reflects the force due to the added displacement in each individual sample.

After testing, a statistical analysis was performed on the collected data, and a model was fit to the data. All variables were considered with their interactions to create possible models to fit the data using multiple linear regression models. The minimum Bayesian information criterion (BIC) was used to determine the best model for each sample set. Case-Influence statistics such as Cook's distance, leverage, and studentized residuals were calculated to ensure that no data was seriously affecting the models. Once the models were created, the modulus of elasticity for each case was calculated using equation 6 in the ASTM D790-17 standard.

Figure 11C:
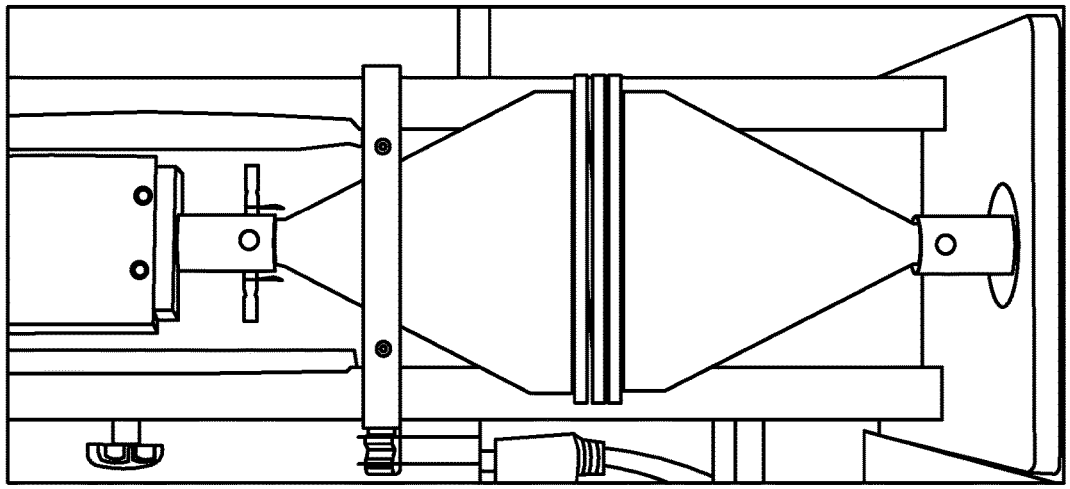
FIGS. 11A-11C illustrate a test setup for compression testing of a deployable Euler spiral connector.
Figure 11B:
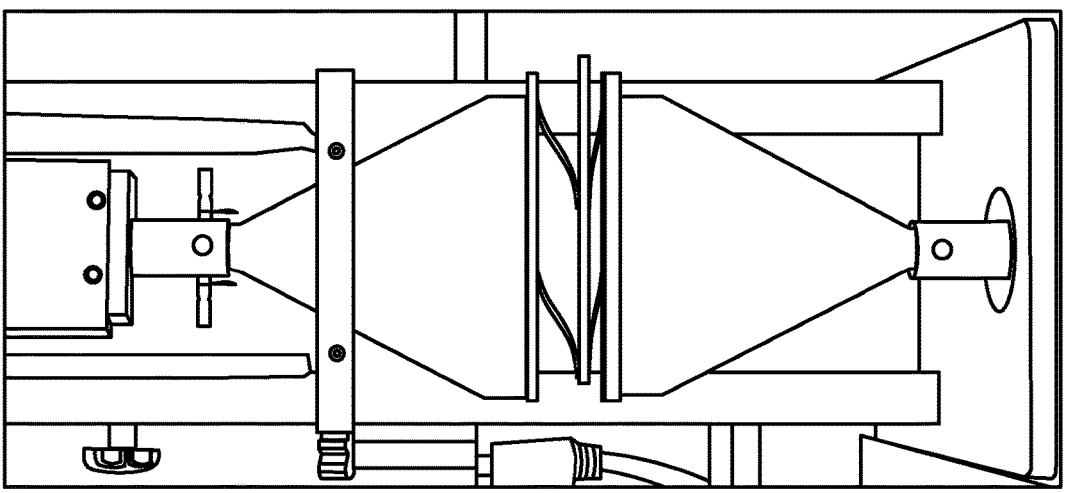
Figure 11A:
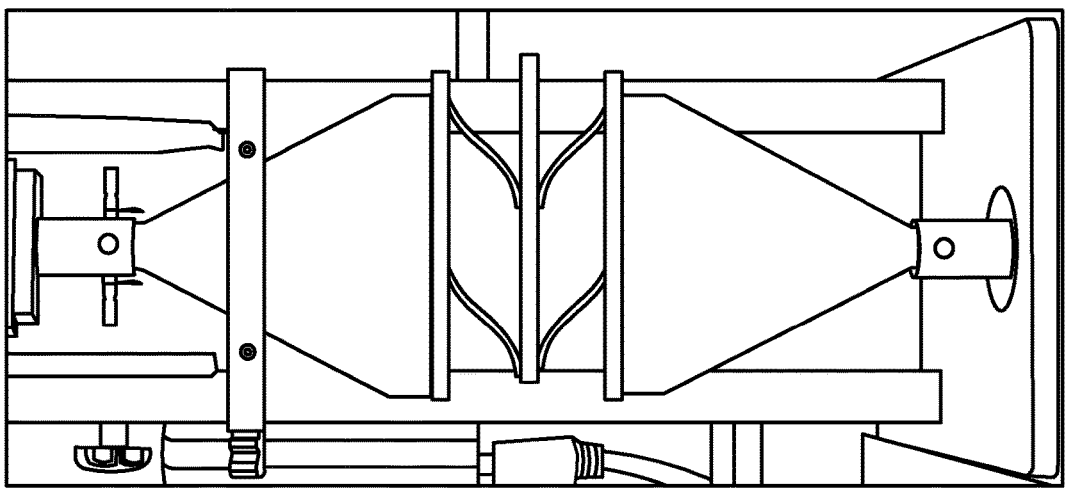

Compression testing to determine maximum stow force was conducted, including testing of DESC prototypes using the test setup shown in FIGS. 11A-11C. DESCs of different curvatures, lengths, and thicknesses were tested. Combinations of the tested DESCs are shown in Table 2. For each curvature-length-thickness combination, three samples were printed. Test samples were made of four DESCs with two parallel DESCs in series with two other parallel DESCs, as shown in FIGS. 11A-11C. Each sample was printed as a single piece. This configuration leads to measured forces of two times the forces needed to displace one DESC. This mechanism setup (four DESCs) was chosen because it allowed the DESCs to be deflected in a guided motion and the bottom surface did not slide relative to the top surface.

To get an accurate force reading (without seeing a force spike due to contact), each test specimen was deflected 95% of its total deflection distance. The force at this value was taken as the maximum force. An Interface SMT1-22 98 N load cell with an uncertainty of 0.03 percent was used to test the DESC samples. The load cell was calibrated after setup, before performing testing, and was zeroed between samples. Each of the samples were tested in order, being compressed to 95% of the total displacement. After being tested, the samples were allowed to relax back to their original positions. The samples were then retested using this procedure ten times each. Testing the three samples in order allowed at least two minutes of relaxation time for each sample before being re-tested.

A statistical analysis was performed on the measurement data collected. All variables were considered with their interactions to create possible models to fit the data using multiple linear regression models. The minimum BIC criteria was again used to determine the best model for each sample set. Case-Influence statistics such as Cook's distance, leverage, and studentized residuals were again calculated to ensure that no data was seriously affecting the models. A 95 percent individual confidence interval was also calculated for the fit.

Figure 12:
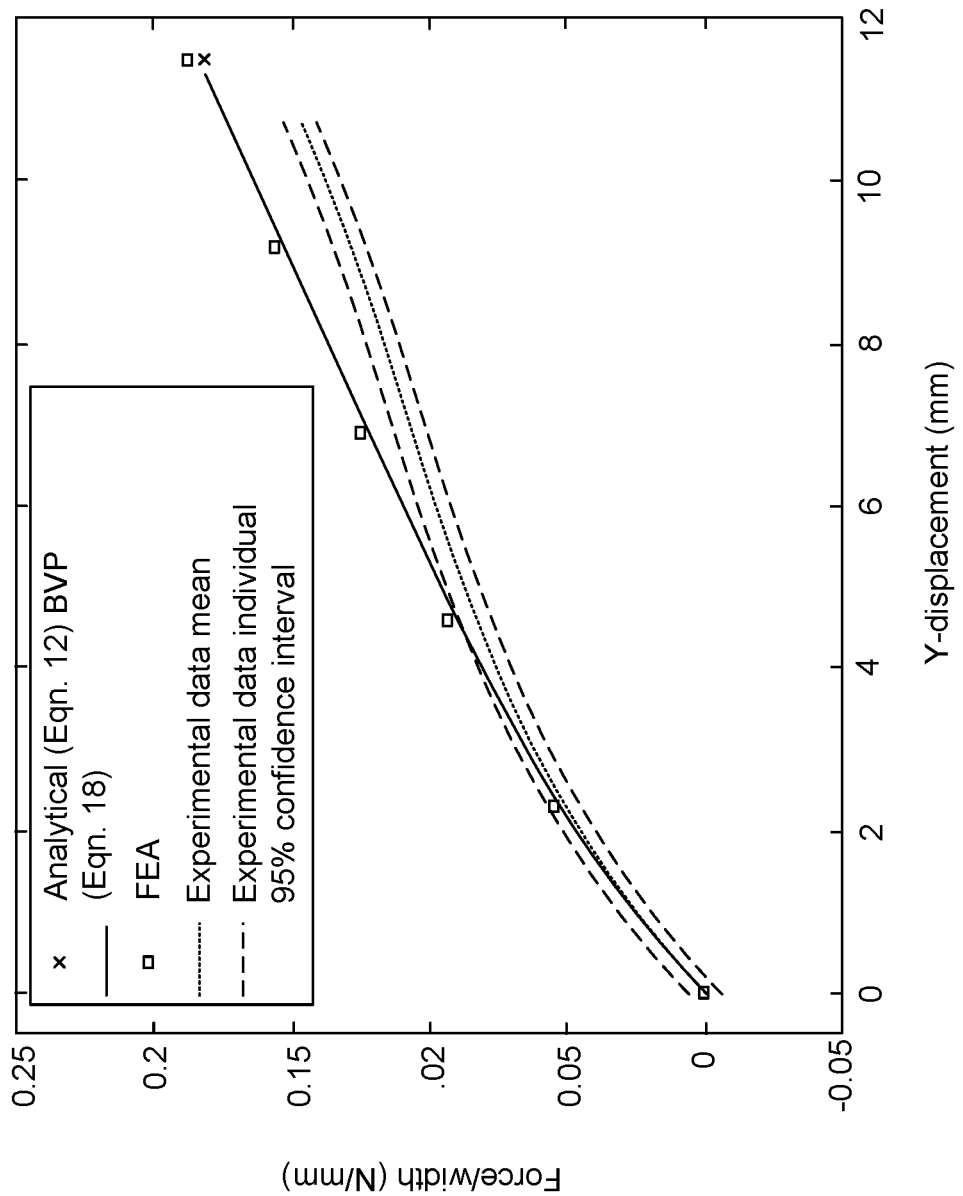
FIG. 12 is a graph illustrating a force deflection curve of a deployable Euler spiral connector.

The mean experimental force per unit width model curve for the 0.19 rad/mm, 19.9 mm long, 1 mm thick DESC flexure shown in FIG. 12. The calculated value found from Equation (12) was also used as the maximum force per unit width value in the boundary value problem (BVP) to determine the force-deflection curve using Equation (18). Both these values are also shown in FIG. 12 along with the FEA data. As a note, in this calculation the full equation of an Euler spiral was used instead of the Taylor Series approximations.

An array with two parallel DESCs on the top row and three parallel DESCs on the bottom row was also tested to verify Equation (13). The force to stow this array was calculated to be 37 N. This configuration was also measured to have a maximum force of 35 N. This yields a percent difference of approximately 6.8% between calculated and measured forces.

FIG. 12 is a graph of the experimental results for the 0.19 rad/mm, 19.9 mm long, 1 mm thick DESC flexure. The results follow the same trend lines as do the force-deflection curves developed using Equation (18) and FEA, although it can be seen that the analytical and experimental trend lines deviate near the end. One source of the difference is that the material properties of the test specimens were approximated to be linear when TPU95 exhibits nonlinear material properties. Although the deviation is slight in the first three configuration cases (0.19 rad/mm, 19.9 mm long, 1 mm thick; 0.19 rad/mm, 19.9 mm long, 2 mm thick; 0.39 rad/mm, 12.8 mm long, 1 mm thick), the experimental results deviate highly from the analytical line for the fourth configuration (0.39 rad/mm, 12.8 mm long, 2 mm thick). This sharp curvature and higher thickness results in strains that cause the nonlinear properties of TPU95 to be exhibited, including localized yielding of the flexures on the outer portions of the flexures due to exceeding the material tensile strength.

Other factors may have also contributed to the deviation. Possible effects include the unmodeled effects of gravity (which have a larger effect for more flexible designs), unequal compression of the different levels, the effects of layers from 3D printing the samples (including delamination of layers, which was observed in at least one sample), manufacturing imperfections due to limitations of the 3D printing process used, and the flexibility of the end connections that were modeled as rigid.

The effects of manufacturing imperfections could have reduced the expected stow force, as evidenced in FIGS. 11A-11C. The bottom set of DESCs compresses fully before the top set. From our assumption that these act as identical springs in series, the top set should compress at the same rate as the bottom set.

While there is some deviation for areas of higher strain, FIG. 12 shows that the motion predicted by the analytical equations and the FEA agree, and that the experimental data shows the same trend of motion, with a deviation primarily due to nonlinear material properties. The difference between the deflections presented for the two analytic solutions is mostly due to the use of the Taylor Series approximation equations to create the spiral in CAD, while the actual equation was used in Equation (18). Even with this difference in methods, the percent difference is still under 2% for both cases.

Two example implementations will be described to demonstrate the application of DESCs, including an example spinal fusion implant and an example ratchet and pawl mechanism. To understand the full benefit of DESCs to the spinal fusion implant, some background on spinal fusion surgical procedures needs will be described.

Spinal fusion implants are a promising design application of DESCs and preliminary designs will be used here to demonstrate their potential use. The efficient stowing and deployment of the flexure can benefit a minimally-invasive spinal fusion procedure.

Spinal fusion is a common procedure in the United States with about 460,000 occurring in 2014. Spinal fusion surgery is performed for a multitude of different disorders. During many spinal fusions, the intervertebral disc is removed. Spinal disc implants are used to maintain the disc height and stabilize the spinal column while bone fusion occurs. In addition to maintaining disc height and providing stabilization, the implant will also ideally provide paths for bone to grow through and fuse together.

Different types of disc implants are used depending on the need and surgical approach technique determined to perform the spinal fusion. Each implant has a specific profile and design that can be implanted using a specific surgical approach with a specific operative size window to perform its needed function. For example, during a posterior lumbar interbody fusion, two devices are placed into the disc space that have smaller cross sections, instead of only one device as in anterior, lateral, and transforaminal fusions. Each of these approaches provides a solution to maintaining disc height and providing stabilization. A larger implant area can result in a larger region of spinal load transfer (e.g., more stability and lower stress), but achieving this usually means a larger implant (and larger incision), or multiple smaller implants.

Because incisions are required to access the spine during fusion surgeries, the size of the incision affects the amount of area that can become infected and affects the time that is required for the incision to heal. The size of the incision is partially determined by the size of equipment (i.e. smaller equipment allows for smaller incisions). While it is desired to have the smallest possible spinal devices to enable the smallest possible incisions, small fusion devices can also lead to subsidence. Subsidence is the sinking of the implant into the surrounding bone due to the differences in mechanical stiffness of the implant in comparison with the supporting bone (i.e., stress overload of the bone). The amount of subsidence (Hsubsidence) that an implant will have is proportional to the forces applied to the implant (F), the difference of the moduli of the implant and the bone ($E_1$, $E_2$), and inversely proportional to the area of the interface between the implant and the bone ($A_{interface}$).

Compliant mechanisms have been used in spinal implants to mimic the natural motion and stiffness of the spine. A deployable implant could help address the seemingly contradictory requirements of a small incision and a large implant that provides stability and reduces subsidence.

Table 3 lists the values determined in the design of the spinal fusion devices. The initial curvatures ($\kappa_0$) and lengths (L) were determined from a desired span of the flexures (x and y) and solving Eqns. (4) and (5). Many of the parameter definitions are shown in FIGS. 5, 13A and 13B.

The compliant spinal device consists of five rigid members connected with DESCs, printed as a single piece. The device employs retractor wires connected to the outermost rigid segments to enable the device to be stowed and released for a controlled deployment. They also allow for the device to be retracted, in the case that the device needs to be moved during placement. The retractor lines are controlled by a rod with a screw head, tight fit into the middle rigid member. The screw head allows a screwdriver to wind and unwind the retractor wire. The tight fit causes friction between the rod and the rigid segment enabling intermediate stow positions, where the device is neither completely deployed nor stowed. This feature allows for the device to be placed with some pre-strain in the DESCs to increase its stiffness. Holes are placed within the rigid segments of the disc implant to allow for bone growth through the device as part of the spinal fusion.

Figure 13A:
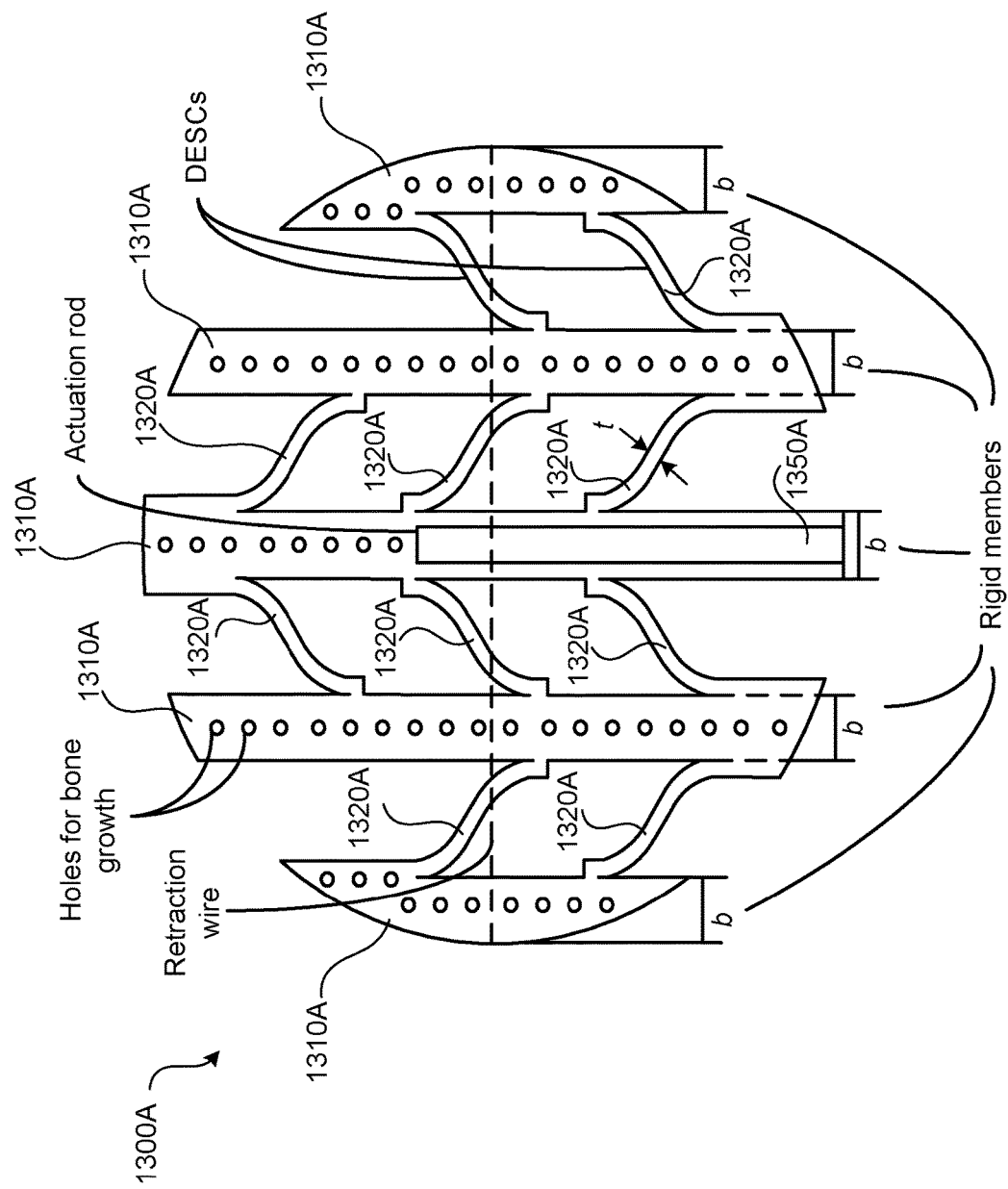
FIG. 13A is a schematic view of an example spine device having a circular cross-section.
Figure 13B:
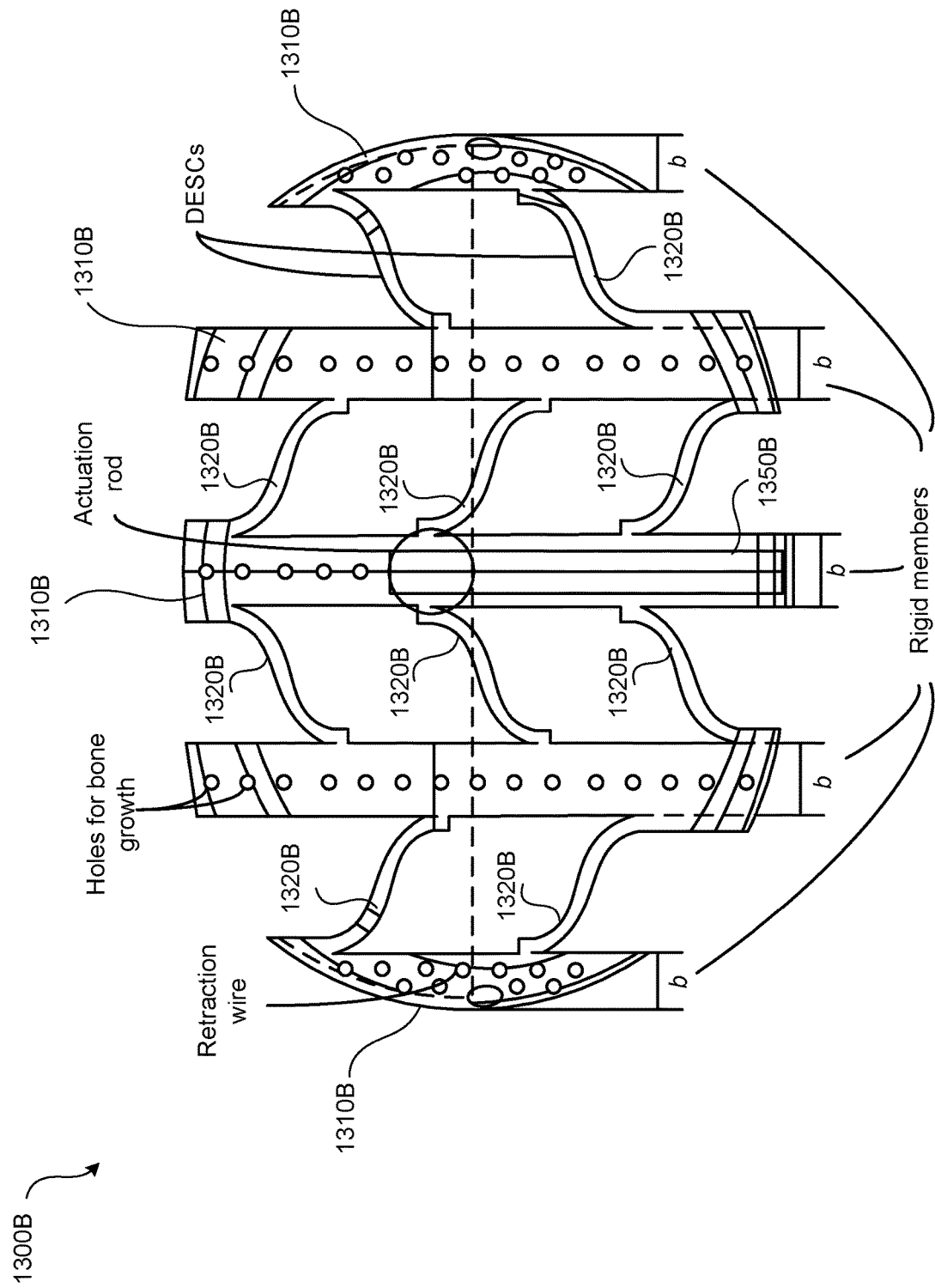
FIG. 13B is a schematic view of an example spine device having an oval cross-section.

FIGS. 13A and 13B are schematic of proof-of-concept prototypes of a spinal implant 1300A using a circular cross-section (FIG. 13A; diameter=92 mm) and a spinal implant 1300B an oval cross-section (FIG. 13B). The oval cross-section is the size of an invertebral disc, approximately an oval of 62 mm wide by 43 mm long. The oval DESC prototype was made by applying the DESC design to the CAD model. Different implant heights and degrees of lordosis may be pre-built into the rigid members 1310A, 1310B so as to re-establish correct anatomical alignment of the spine upon deployment. Flexures defining the compliant connectors 1320A, 1320B of 1 mm thickness were chosen as they do not exceed the tensile strength of the POLYFLEX 3D-printing filament during stowing of the devices. The values in Table 3 were used to calculate the force to stow the disc devices and their maximum stresses. Additionally, the parameters in Table 3 were used in the FEA and experimental models to validate the analytical models presented. Other parameters were also used to compare the presented equations for many different cases. The device(s) 1300A, 1300B will be actuated less than ten times so high cycle fatigue is not considered.

TABLE 3

| Configuration | Circular | Oval | Units |
|---|---|---|---|
| Input Parameters | | | |
| Circle Diameter (d) | 92 | — | mm |
| Oval Width (w) | — | 62 | mm |
| Oval Height (h) | — | 43 | mm |
| Avg Rigid Segment Width (b) | 7.58 | 4.57 | mm |
| Depth of Device (d) | 8 | 17.37 | mm |
| Thickness of | 2 | 1.03 | mm |

TABLE 3-continued

| Configuration | Circular | Oval | Units |
|---|---|---|---|
| DESCs (t) | | | |
| Initial Curvature ($\kappa_0$) | 0.19 | 0.39 | mm$^{-1}$ |
| Arc Length of DESCs (L) | 19.9 | 12.8 | mm |
| Horizontal Span (x) | 11.5 | 8.65 | mm |
| Vertical Span (y) | 15 | 7.61 | mm |
| Number of DESCs in Row 1 ($n_1$) | 2 | 2 | — |
| Number of DESCs in Row 2 ($n_2$) | 3 | 3 | — |
| Flex. Modulus of Elasticity (E) | 103 | 114 | MPa |
| POLYFLEX Material Tensile Strength[40] ($S_T$) | 29.0 ± 2.8 | 29.0 ± 2.8 | MPa |

TABLE 4

| Configuration | Circular | Oval | Units |
|---|---|---|---|
| Calculated Parameters | | | |
| Deployed Area ($A_{top_{deployed}}$) | 6648 | 2233 | mm$^2$ |
| Compressed Width (W) | 45.90 | 26.96 | mm |
| Stowed Area ($A_{front_{stowed}}$) | 367.2 | 468.3 | mm$^2$ |
| Force to Stow One Side (F) | 3.16 | 1.39 | N/mm |
| Maximum Stress ($\sigma_{max}$) | 19.64 | 22.8 | MPa |

FIGS. 14A(1)-14B(2) show the proof-of-concept prototype spinal fusion implants with incorporated DESCs in the deployed position and the stowed position, respectively. FIG. 14A(1) shows the circular cross-section spinal implant 1300A and FIG. 14A(2) shows the oval cross-section spinal implant 1300B in the deployed position. FIG. 14B(1) shows the circular cross-section spinal implant 1300A and FIG. 14B(2) shows the oval cross-section spinal implant 1300B in the stowed position. Table 4 lists the results calculated for the DESC devices. Note that because the devices 1300A, 1300B are actuated from the center rigid member 1310A, 1310B, the DESCs defining the compliant connectors 1320A, 1320B on either side of the center rigid member 1310A, 1310B require the same force. However, to actuate the central rod 1350A, 1350B, the torque needed would be equal to 2F multiplied by the distance to the center of the central rod 1350A, 1350B (d/2). When the physical prototypes compressed widths were measured, the widths for the circular cross-section spinal implant 1300A and the oval cross-section spinal implant 1300B were approximately 46.0 and 27.8 mm, respectively. The differences in the measured and calculated values are largely due to the tolerances of the manufacturing processes and nonlinear material properties. Both physical prototypes, shown in FIGS. 14A(1)-14B(2), were made of POLYFLEX 3D-printing filament (TPU95).

The results from Table 4 show that a device can be created that stows efficiently to allow for smaller incisions, while still being able to fill the desired deployed area. These results also show that the flexure parameters (width, thickness, length, initial curvature) can be adjusted to create a design with the desired stow force and stress that remains below the allowable stress to prevent failure. Additionally, the device presented here shows that the stored strain energy in the flexures can be used to help deploy the spinal fusion implant and provide some additional desired stiffening to the device.

Although the spinal fusion implant discussed here was the primary motivation for the development of DESCs, they could be used in other applications, including two noted below.

FIGS. 15A-15C show a linear ratchet mechanism 1500 with DESCs. The pawl 1550 in the mechanism 1500 was designed using DESCs defining compliant connectors 1520, to attain the needed motion for ratcheting and was printed as a single piece. In FIG. 15A, the pawl 1550 is removed from the rack 1560. As the pawl 1550 is pushed through the rack 1560 in FIG. 15B, the DESCs 1520 compress flat, allowing teeth 1555 of the pawl 1550 to move to the next set of teeth 1565 in the rack 1560. The DESCs defining the compliant connectors 1520 expand back out to lock the mechanism 1500 into the new position, as shown in FIG. 15C. The prototype was made of polylactic acid (PLA) with a flexural modulus of elasticity of 3.5 GPa. The length of the DESCs defining the compliant connectors 1520 in the mechanism is 25.4 mm with an initial curvature of 0.041 $mm^{-1}$ and thickness of 0.8 mm. The force needed to compress the DESCs defining the compliant connectors 1520 on one side of the pawl 1550 is approximately 1.45 N/mm. As discussed above, a desired force can be determined by changing the initial curvature, length, or thickness of the DESCs or changing the material.

Because the DESCs will lay flat when fully stowed and can be designed to lay flat at a specific force, they can be used to design mechanisms where the desired final position is flat. This gives the designer the ability to design the device for a specific desired force. Other applications of DESC flexures include use in mechanisms that absorb shock loads, such as in ski or snowboard bindings. In its most general form, the DESC can be viewed as a fully compact spring which could have broad applications that extend well beyond the field of mechanism design.

The concept of the Euler spiral has been applied to design compliant connections that will lay flat when stowed, allowing compact stowing and the use of the stored strain energy for actuation. This is accomplished by solving the presented equations for the desired spans to determine the initial curvature, $\kappa_0$, and length, $L$, of the connections. Taylor Series approximations were used to solve for the desired variables to design the DESCs. Equations to determine the force-deflection behavior of these flexures and the maximum stress predicted were also presented. These equations show that the force and stress is dependent on (and can be tailored by changing) the flexure parameters. The results from these equations, FEA, and experimental data were compared and show good agreement.

A spinal disc implant has been presented as an application for DESCs. The determined forces needed to stow and accompanying stresses of two spinal devices showed that DESCs can be beneficial to the stowability and force-deflection design of these implants and show promise for other applications.

Specific structural and functional details disclosed herein are merely representative for purposes of describing example embodiments. Example embodiments, however, may be embodied in many alternate forms and should not be construed as limited to only the embodiments set forth herein.

The terminology used herein is for the purpose of describing particular embodiments only and is not intended to be limiting of the embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of the stated features, steps, operations, elements, and/or components, but do not preclude the presence or addition of one or more other features, steps, operations, elements, components, and/or groups thereof.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present. As used herein the term "and/or" includes any and all combinations of one or more of the associated listed items.

Spatially relative terms, such as "beneath," "below," "lower," "above," "upper," and the like, may be used herein for ease of description to describe one element or feature in relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 70 degrees or at other orientations) and the spatially relative descriptors used herein may be interpreted accordingly.

Example embodiments of the concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the described concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

Unless otherwise defined, the terms (including technical and scientific terms) used herein have the same meaning as commonly understood by one of ordinary skill in the art to which these concepts belong. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

While certain features of the described implementations have been illustrated as described herein, many modifications, substitutions, changes, and equivalents will now occur to those skilled in the art. It is, therefore, to be understood that the appended claims are intended to cover such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components, and/or features of the different implementations described.

What is claimed is:

1. An expandable implantable device, comprising:
   a plurality of support members; and
   a plurality of compliant connectors connecting adjacent support members of the plurality of support members,
   wherein the plurality of support members includes a planar arrangement of longitudinal members that are movable relative to each other, between a stowed configuration for insertion of the expandable implantable device into an intervertebral implant location, and a deployed configuration for expansion of the expandable implantable device at the intervertebral implant location,
   wherein, in the stowed configuration,
      each of the plurality of support members abuts an adjacent support member of the plurality of support members, with central longitudinal axes of the plurality of support members aligned in a first direction, and
      the plurality of compliant connectors are arranged in a planar configuration between the adjacent support members, with central longitudinal axes of each of the plurality of compliant connectors aligned in the first direction, between respective pairs of adjacent support members.

2. The expandable implantable device of claim 1, wherein the plurality of compliant connectors maintains a relative position of the plurality of support members so as to maintain the expandable implantable device in the stowed configuration or the deployed configuration.

3. The expandable implantable device of claim 1, wherein the stowed configuration is a fully stowed configuration in which each of the plurality of support members abuts at least one adjacent support member, such that a volume between adjacent support members of the plurality of support members is occupied by the plurality of compliant connectors.

4. The expandable implantable device of claim 3, wherein the deployed configuration is a fully deployed configuration in which the plurality of compliant connectors are fully expanded to span spaces formed between the adjacent support members, wherein the fully deployed configuration corresponds to a maximum overall volume of the expandable implantable device.

5. The expandable implantable device of claim 4, wherein the plurality of support members are movable to a plurality of intermediate configurations between the fully stowed configuration and the fully deployed configuration.

6. The expandable implantable device of claim 5, wherein the plurality of support members are configured to move, between the stowed configuration and the deployed configuration, in response to an externally applied force.

7. The expandable implantable device of claim 5, wherein the plurality of support members are configured to move, from the fully stowed configuration to an intermediate configuration of the plurality of intermediate configurations, in response to a release of strain energy stored by the plurality of compliant connectors.

8. The expandable implantable device of claim 7, wherein the plurality of support members are configured to move from the intermediate configuration towards the fully deployed configuration in response to an externally applied force.

9. The expandable implantable device of claim 3, wherein, in the fully stowed configuration, the volume between adjacent support members of the plurality of support members is substantially fully occupied by the plurality of compliant connectors between the adjacent support members, such that a distance between adjacent support members of the plurality of support members corresponds to a thickness of the plurality of compliant connectors extending between the adjacent support members, and the fully stowed configuration corresponds to a minimum overall volume of the expandable implantable device.

10. The expandable implantable device of claim 1, wherein each of the plurality of compliant connectors is configured to store strain energy in the stowed configuration of the expandable implantable device, and wherein the plurality of compliant connectors are configured to expand and separate the plurality of support members in response to a release of the strain energy stored by the plurality of compliant connectors.

11. The expandable implantable device of claim 1, wherein each of the plurality of compliant connectors has an Euler spiral shape.

12. The expandable implantable device of claim 1, wherein the plurality of compliant connectors includes a plurality of Deployable Euler Spiral Connectors (DESCs).

13. The expandable implantable device of claim 1, wherein, in the stowed configuration,
   a first side portion of each of the plurality of compliant connectors contacts a corresponding side portion of a first support member of a pair of adjacent support members of the plurality of support members, and
   a second side portion of each of the plurality of compliant connectors abuts a corresponding side portion of a second support member of the pair of adjacent support members of the plurality of support members.

14. The expandable implantable device of claim 13, wherein, in the stowed configuration, the central longitudinal axes of the plurality of support members and the central longitudinal axes of the plurality of compliant connectors are arranged substantially in parallel.

15. The expandable implantable device of claim 1, wherein the plurality of support members are configured to move in a second direction relative to each other to move from the stowed configuration to the deployed configuration, and to move in a third direction relative to each other to move from the deployed configuration to the stowed configuration, wherein the second direction is substantially orthogonal to the first direction, and the third direction is substantially opposite the second direction.

16. The expandable implantable device of claim 1, wherein, in the stowed configuration, side portions of the plurality of compliant connectors contact a corresponding side portion of an adjacent support member of the plurality of support members.

17. The expandable implantable device of claim 1, wherein the plurality of support members includes a planar arrangement of rigid longitudinal members, including:
 a central support member; and
 a plurality of auxiliary support members arranged symmetrically about the central support member.

18. The expandable implantable device of claim 1, wherein the expandable implantable device is a spinal implant implantable at the intervertebral implant location between adjacent vertebrae of a spine of a patient, and wherein, in the deployed configuration, the plurality of support members of the expandable implantable device are configured to support the adjacent vertebrae of the spine and to maintain a relative position of the adjacent vertebrae.

19. The expandable implantable device of claim 18, wherein, in the deployed configuration, a height and a degree of lordosis of the plurality of support members of the expandable implantable device are configured to maintain an anatomical alignment of the spine.

20. An expandable implantable device, comprising:
 a plurality of support members; and
 a plurality of compliant connectors connecting pairs of adjacent support members of the plurality of support members,
 wherein the plurality of support members are movable relative to each other, between a stowed configuration for insertion of the expandable implantable device into an intervertebral implant location, and a deployed configuration for expansion of the expandable implantable device at the intervertebral implant location, and
 wherein, in the stowed configuration, each of the plurality of compliant connectors is arranged in a planar configuration between a corresponding pair of adjacent support members, with a first side portion of each of the plurality of compliant connectors abutting a corresponding side portion of a first support member of the corresponding pair of adjacent support members of the plurality of support members, and a second side portion of each of the plurality of compliant connectors abutting a corresponding side portion of a second support member of the corresponding pair of adjacent support members of the plurality of support members.

21. The expandable implantable device of claim 20, wherein the plurality of support members includes a planar arrangement of rigid longitudinal members, wherein, in the stowed configuration,
 central longitudinal axes of the plurality of support members are arranged substantially in parallel with each other, and
 central longitudinal axes of the plurality of compliant connectors are arranged in parallel with the central longitudinal axes of the plurality of support members.

22. The expandable implantable device of claim 21, wherein the plurality of support members are configured to move in a first direction relative to each other to move from the stowed configuration to the deployed configuration, and to move in a second direction relative to each other to move from the deployed configuration to the stowed configuration, wherein the second direction is substantially opposite the first direction, and the first direction and the second direction are substantially orthogonal to the central longitudinal axes of the plurality of support members.

23. The expandable implantable device of claim 20, wherein the stowed configuration is a fully stowed configuration in which each of the plurality of support members abuts at least one adjacent support member, such that a volume between pairs of adjacent support members is substantially fully occupied by the plurality of compliant connectors and the fully stowed configuration corresponds to a minimum overall volume of the expandable implantable device.

24. The expandable implantable device of claim 4, wherein the deployed configuration is a fully deployed configuration in which the plurality of compliant connectors are fully expanded to span spaces formed between the adjacent support members, wherein the fully deployed configuration corresponds to a maximum overall volume of the expandable implantable device.

25. The expandable implantable device of claim 20, wherein the expandable implantable device is a spinal implant implantable at the intervertebral implant location between adjacent vertebrae of a spine of a patient, and wherein, in the deployed configuration, the plurality of support members of the expandable implantable device are configured to support the adjacent vertebrae of the spine and to maintain a relative position of the adjacent vertebrae.

26. The expandable implantable device of claim 25, wherein, in the deployed configuration, a height and a degree of lordosis of the plurality of support members of the expandable implantable device are configured to maintain an anatomical alignment of the spine.

* * * * *

UNITED STATES PATENT AND TRADEMARK OFFICE
CERTIFICATE OF CORRECTION

| | | |
|---|---|---|
| PATENT NO. | : 12,036,129 B2 | Page 1 of 1 |
| APPLICATION NO. | : 17/445017 | |
| DATED | : July 16, 2024 | |
| INVENTOR(S) | : Howell et al. | |

It is certified that error appears in the above-identified patent and that said Letters Patent is hereby corrected as shown below:

In the Claims

In Column 22, Claim 24, Line 27, delete "4," and insert -- 20, --, therefor.

Signed and Sealed this
Twenty-seventh Day of August, 2024

Katherine Kelly Vidal
*Director of the United States Patent and Trademark Office*